US012751676B2

(12) United States Patent
Ren et al.

(10) Patent No.: US 12,751,676 B2
(45) Date of Patent: Oct. 6, 2026

(54) WIDE ANGLE AUTOMATIC EXPOSURE CONTROL IN TOMOSYNTHESIS

(71) Applicant: Hologic, Inc., Marlborough, MA (US)

(72) Inventors: Baorui Ren, Andover, MA (US); Richard Amos, Wilmington, DE (US)

(73) Assignee: Hologic, Inc., Marlborough, MA (US)

( * ) Notice: Subject to any disclaimer, the term of this patent is extended or adjusted under 35 U.S.C. 154(b) by 82 days.

(21) Appl. No.: 18/875,473

(22) PCT Filed: Jun. 30, 2023

(86) PCT No.: PCT/US2023/069518

§ 371 (c)(1),
(2) Date: Dec. 16, 2024

(87) PCT Pub. No.: WO2024/011080

PCT Pub. Date: Jan. 11, 2024

(65) Prior Publication Data

US 2026/0020827 A1 Jan. 22, 2026

Related U.S. Application Data

(60) Provisional application No. 63/358,350, filed on Jul. 5, 2022.

(51) Int. Cl.
*A61B 6/02* (2006.01)
*A61B 6/00* (2024.01)
(Continued)

(52) U.S. Cl.
CPC ............ *A61B 6/025* (2013.01); *A61B 6/0435* (2013.01); *A61B 6/488* (2013.01); *A61B 6/502* (2013.01);
(Continued)

(58) Field of Classification Search
CPC ....... A61B 6/025; A61B 6/0435; A61B 6/488; A61B 6/502; A61B 6/5258; A61B 6/542;
(Continued)

(56) References Cited

U.S. PATENT DOCUMENTS 3,365,575 A 1/1968 Strax
3,502,878 A 3/1970 Stewart
(Continued)

FOREIGN PATENT DOCUMENTS

CN 1711052 A 12/2005
CN 100362964 1/2008
(Continued)

OTHER PUBLICATIONS

PCT International Preliminary Report on Patentability in Application PCT/US2023/069518, mailed Jan. 16, 2025, 9 pages.
(Continued)

*Primary Examiner* — Mark R Gaworecki
(74) *Attorney, Agent, or Firm* — Merchant & Gould P.C.

(57) ABSTRACT

The present application discloses a system and method to calculate the automatic exposure control (AEC) calibrated dosage for tomosynthesis sweeps. For example, reference images may be acquired, and corresponding reference detector count maps may be generated and stored for a plurality of projection angles using the tomosynthesis imaging system. The tomosynthesis imaging system may then acquire a scout image using a scout dosage, identify the densest region within the scout image, and calculated the average detector count values associated with the densest region. The AEC calibrated dosage can be calculated based on a ratio of the average reference detector count values, corresponding to the detector count values of pixels with a corresponding densest region of the reference image, and the calculated average detector count values.

20 Claims, 10 Drawing Sheets

(51) Int. Cl.
*A61B 6/04* (2006.01)
*A61B 6/50* (2024.01)
*A61B 6/58* (2024.01)

(52) U.S. Cl.
CPC .............. *A61B 6/542* (2013.01); *A61B 6/545* (2013.01); *A61B 6/582* (2013.01); *A61B 6/583* (2013.01); *A61B 6/584* (2013.01); *A61B 6/5258* (2013.01)

(58) Field of Classification Search
CPC ......... A61B 6/545; A61B 6/582; A61B 6/583; A61B 6/584
See application file for complete search history.

(56) References Cited

U.S. PATENT DOCUMENTS

| | | | |
|---|---|---|---|
| 3,578,971 | A | 5/1971 | Lasky |
| 3,863,073 | A | 1/1975 | Wagner |
| 3,971,950 | A | 7/1976 | Evans et al. |
| 3,973,126 | A | 8/1976 | Redington et al. |
| 4,160,906 | A | 7/1979 | Daniels et al. |
| 4,212,306 | A | 7/1980 | Mahmud |
| 4,259,585 | A | 3/1981 | Novak et al. |
| 4,310,766 | A | 1/1982 | Finkenzeller et al. |
| 4,380,086 | A | 4/1983 | Vagi |
| 4,496,557 | A | 1/1985 | Malen et al. |
| 4,513,433 | A | 4/1985 | Weiss et al. |
| 4,542,521 | A | 9/1985 | Hahn et al. |
| 4,559,641 | A | 12/1985 | Caugant et al. |
| 4,599,738 | A | 7/1986 | Panetta et al. |
| 4,658,409 | A | 4/1987 | Summ |
| 4,662,379 | A | 5/1987 | Macovski |
| 4,706,269 | A | 11/1987 | Reina et al. |
| 4,721,856 | A | 1/1988 | Saotome et al. |
| 4,744,099 | A | 5/1988 | Huettenrauch et al. |
| 4,752,948 | A | 6/1988 | MacMahon |
| 4,760,589 | A | 7/1988 | Siczek |
| 4,763,343 | A | 8/1988 | Yanaki |
| 4,773,086 | A | 9/1988 | Fujita et al. |
| 4,773,087 | A | 9/1988 | Plewes |
| 4,819,258 | A | 4/1989 | Kleinman et al. |
| 4,821,727 | A | 4/1989 | Levene et al. |
| 4,962,515 | A | 10/1990 | Kopans |
| 4,969,174 | A | 11/1990 | Scheid et al. |
| 4,989,227 | A | 1/1991 | Tirelli et al. |
| 5,018,176 | A | 5/1991 | Romeas et al. |
| RE33,634 | E | 7/1991 | Yanaki |
| 5,029,193 | A | 7/1991 | Saffer |
| 5,051,904 | A | 9/1991 | Griffith |
| 5,078,142 | A | 1/1992 | Siczek et al. |
| 5,099,503 | A | 3/1992 | Strommer |
| 5,163,075 | A | 11/1992 | Lubinsky et al. |
| 5,164,976 | A | 11/1992 | Scheid et al. |
| 5,199,056 | A | 3/1993 | Darrah |
| 5,212,637 | A | 5/1993 | Saxena |
| 5,240,011 | A | 8/1993 | Assa |
| 5,256,370 | A | 10/1993 | Slattery |
| 5,274,690 | A | 12/1993 | Burke |
| 5,289,520 | A | 2/1994 | Pellegrino et al. |
| 5,291,539 | A | 3/1994 | Thumann et al. |
| 5,313,510 | A | 5/1994 | Ebersberger |
| 5,335,257 | A | 8/1994 | Stunberg |
| 5,359,637 | A | 10/1994 | Webber |
| 5,365,562 | A | 11/1994 | Toker |
| 5,415,169 | A | 5/1995 | Siczek et al. |
| 5,426,685 | A | 6/1995 | Pellegrino et al. |
| 5,452,367 | A | 9/1995 | Bick et al. |
| 5,469,429 | A | 11/1995 | Yamazaki et al. |
| 5,506,877 | A | 4/1996 | Niklason et al. |
| 5,526,394 | A | 6/1996 | Siczek et al. |
| 5,528,658 | A | 6/1996 | Hell |
| 5,539,797 | A | 7/1996 | Heidsieck et al. |
| 5,553,111 | A | 9/1996 | Moore et al. |
| 5,590,271 | A | 12/1996 | Klinker |
| 5,592,562 | A | 1/1997 | Rooks |
| 5,594,769 | A | 1/1997 | Pellegrino et al. |
| 5,596,200 | A | 1/1997 | Sharma et al. |
| 5,598,454 | A | 1/1997 | Franetzke et al. |
| 5,609,152 | A | 3/1997 | Pellegrino et al. |
| 5,627,869 | A | 5/1997 | Andrew et al. |
| 5,657,362 | A | 8/1997 | Giger et al. |
| 5,668,844 | A | 9/1997 | Webber |
| 5,668,889 | A | 9/1997 | Hara |
| 5,706,327 | A | 1/1998 | Adamkowski et al. |
| 5,719,952 | A | 2/1998 | Rooks |
| 5,735,264 | A | 4/1998 | Siczek et al. |
| 5,769,086 | A | 6/1998 | Ritchart et al. |
| 5,803,912 | A | 9/1998 | Siczek et al. |
| 5,818,898 | A | 10/1998 | Tsukamoto et al. |
| 5,828,722 | A | 10/1998 | Ploetz et al. |
| 5,841,829 | A | 11/1998 | Dolazza |
| 5,844,965 | A | 12/1998 | Galkin |
| 5,864,146 | A | 1/1999 | Karellas |
| 5,872,828 | A | 2/1999 | Niklason et al. |
| 5,878,104 | A | 3/1999 | Ploetz |
| 5,896,437 | A | 4/1999 | Ploetz |
| 5,941,832 | A | 8/1999 | Tumey et al. |
| 5,970,118 | A | 10/1999 | Sokolov |
| 5,983,123 | A | 11/1999 | Shmulewitz |
| 5,986,662 | A | 11/1999 | Argiro et al. |
| 5,999,836 | A | 12/1999 | Nelson et al. |
| 6,005,907 | A | 12/1999 | Ploetz |
| 6,022,325 | A | 2/2000 | Siczek et al. |
| 6,075,879 | A | 6/2000 | Roehrig et al. |
| 6,091,841 | A | 7/2000 | Rogers et al. |
| 6,137,527 | A | 10/2000 | Abdel-Malek et al. |
| 6,141,398 | A | 10/2000 | He et al. |
| 6,149,301 | A | 11/2000 | Kautzer et al. |
| 6,167,115 | A | 12/2000 | Inoue |
| 6,175,117 | B1 | 1/2001 | Komardin et al. |
| 6,196,715 | B1 | 3/2001 | Nambu et al. |
| 6,207,958 | B1 | 3/2001 | Giakos |
| 6,216,540 | B1 | 4/2001 | Nelson et al. |
| 6,219,059 | B1 | 4/2001 | Argiro |
| 6,233,473 | B1 | 5/2001 | Shepherd et al. |
| 6,243,441 | B1 | 6/2001 | Zur |
| 6,244,507 | B1 | 6/2001 | Garland |
| 6,256,369 | B1 | 7/2001 | Lai |
| 6,256,370 | B1 | 7/2001 | Yavuz |
| 6,272,207 | B1 | 8/2001 | Tang |
| 6,289,235 | B1 | 9/2001 | Webber et al. |
| 6,292,530 | B1 | 9/2001 | Yavus et al. |
| 6,293,282 | B1 | 9/2001 | Lemelson |
| 6,327,336 | B1 | 12/2001 | Gingold et al. |
| 6,341,156 | B1 | 1/2002 | Baetz et al. |
| 6,345,194 | B1 | 2/2002 | Nelson et al. |
| 6,375,352 | B1 | 4/2002 | Hewes et al. |
| 6,411,836 | B1 | 6/2002 | Patel et al. |
| 6,415,015 | B2 | 7/2002 | Nicolas et al. |
| 6,418,189 | B1 | 7/2002 | Schafer |
| 6,442,288 | B1 | 8/2002 | Haerer et al. |
| 6,459,925 | B1 | 10/2002 | Nields et al. |
| 6,480,565 | B1 | 11/2002 | Ning |
| 6,490,476 | B1 | 12/2002 | Townsend et al. |
| 6,501,819 | B2 | 12/2002 | Unger et al. |
| 6,542,575 | B1 | 4/2003 | Schubert |
| 6,553,096 | B1 | 4/2003 | Zhou et al. |
| 6,556,655 | B1 | 4/2003 | Chichereau et al. |
| 6,574,304 | B1 | 6/2003 | Hsieh et al. |
| 6,574,629 | B1 | 6/2003 | Cooke, Jr. et al. |
| 6,597,762 | B1 | 7/2003 | Ferrant et al. |
| 6,611,575 | B1 | 8/2003 | Alyassin et al. |
| 6,620,111 | B2 | 9/2003 | Stephens et al. |
| 6,626,849 | B2 | 9/2003 | Huitema et al. |
| 6,633,674 | B1 | 10/2003 | Barnes et al. |
| 6,638,235 | B2 | 10/2003 | Miller et al. |
| 6,645,520 | B2 | 11/2003 | Hsu et al. |
| 6,647,092 | B2 | 11/2003 | Eberhard et al. |
| 6,744,848 | B2 | 6/2004 | Stanton et al. |
| 6,748,044 | B2 | 6/2004 | Sabol et al. |
| 6,751,285 | B2 | 6/2004 | Eberhard et al. |
| 6,758,824 | B1 | 7/2004 | Miller et al. |
| 6,813,334 | B2 | 11/2004 | Koppe et al. |

(56) References Cited

U.S. PATENT DOCUMENTS

| | | | |
|---|---|---|---|
| 6,845,146 | B2 | 1/2005 | Rcik et al. |
| 6,882,700 | B2 | 4/2005 | Wang et al. |
| 6,885,724 | B2 | 4/2005 | Li et al. |
| 6,895,076 | B2 | 5/2005 | Halsmer |
| 6,909,790 | B2 | 6/2005 | Tumey et al. |
| 6,909,792 | B1 | 6/2005 | Carrott et al. |
| 6,912,319 | B1 | 6/2005 | Barnes et al. |
| 6,940,943 | B2 | 9/2005 | Claus et al. |
| 6,950,493 | B2 | 9/2005 | Besson |
| 6,957,099 | B1 | 10/2005 | Arnone et al. |
| 6,970,531 | B2 | 11/2005 | Eberhard et al. |
| 6,978,040 | B2 | 12/2005 | Berestov |
| 6,987,831 | B2 | 1/2006 | Ning |
| 6,999,552 | B2 | 2/2006 | Tsuji |
| 6,999,554 | B2 | 2/2006 | Mertelmeier |
| 7,001,071 | B2 | 2/2006 | Deuringer |
| 7,016,461 | B2 | 3/2006 | Rotondo |
| 7,110,490 | B2 | 9/2006 | Eberhard et al. |
| 7,110,502 | B2 | 9/2006 | Tsuji |
| 7,116,749 | B2 | 10/2006 | Besson |
| 7,120,283 | B2 | 10/2006 | Thieret et al. |
| 7,123,684 | B2 | 10/2006 | Jing et al. |
| 7,127,091 | B2 | 10/2006 | Op De Beek et al. |
| 7,142,633 | B2 | 11/2006 | Eberhard et al. |
| 7,190,758 | B2 | 3/2007 | Hagiwara |
| 7,206,462 | B1 | 4/2007 | Betke |
| 7,218,766 | B2 | 5/2007 | Eberhard |
| 7,244,063 | B2 | 7/2007 | Eberhard |
| 7,245,692 | B2 | 7/2007 | Lu et al. |
| 7,245,694 | B2 | 7/2007 | Jing et al. |
| 7,286,645 | B2 | 10/2007 | Freudenberger |
| 7,302,031 | B2 | 11/2007 | Hjarn et al. |
| 7,315,607 | B2 | 1/2008 | Ramsauer |
| 7,319,735 | B2 | 1/2008 | Defreitas et al. |
| 7,319,736 | B2 | 1/2008 | Rotondo |
| 7,323,692 | B2 | 1/2008 | Rowlands et al. |
| 7,331,264 | B2 | 2/2008 | Ozawa |
| 7,356,113 | B2 | 4/2008 | Wu |
| 7,430,272 | B2 | 9/2008 | Jing et al. |
| 7,443,949 | B2 | 10/2008 | Defreitas et al. |
| 7,515,682 | B2 | 4/2009 | Li et al. |
| 7,577,282 | B2 | 8/2009 | Gkanatsios et al. |
| 7,583,786 | B2 | 9/2009 | Jing et al. |
| 7,609,806 | B2 | 10/2009 | Defreitas et al. |
| 7,616,731 | B2 | 11/2009 | Pack |
| 7,616,801 | B2 | 11/2009 | Gkanatsios et al. |
| 7,630,531 | B2 | 12/2009 | Chui |
| 7,630,533 | B2 | 12/2009 | Ruth et al. |
| 7,656,994 | B2 | 2/2010 | Eberhard et al. |
| 7,688,940 | B2 | 3/2010 | Defreitas et al. |
| 7,697,660 | B2 | 4/2010 | Ning |
| 7,702,142 | B2 | 4/2010 | Ren et al. |
| 7,742,796 | B2 | 6/2010 | Eberhard et al. |
| 7,760,853 | B2 | 7/2010 | Jing et al. |
| 7,760,924 | B2 | 7/2010 | Ruth et al. |
| 7,778,388 | B2 | 8/2010 | Sendai |
| 7,792,245 | B2 | 9/2010 | Hitzke et al. |
| 7,831,296 | B2 | 11/2010 | Defreitas et al. |
| 7,839,979 | B2 | 11/2010 | Hauttmann |
| 7,869,563 | B2 | 1/2011 | Defreitas et al. |
| 7,881,428 | B2 | 2/2011 | Jing et al. |
| 7,885,384 | B2 | 2/2011 | Mannar |
| 7,894,646 | B2 | 2/2011 | Shirahata et al. |
| 7,916,915 | B2 | 3/2011 | Gkanatsios et al. |
| 7,949,091 | B2 | 5/2011 | Jing et al. |
| 7,986,765 | B2 | 7/2011 | Defreitas et al. |
| 7,991,106 | B2 | 8/2011 | Ren et al. |
| 8,005,184 | B2 | 8/2011 | Chen |
| 8,031,834 | B2 | 10/2011 | Ludwig |
| 8,131,049 | B2 | 3/2012 | Ruth et al. |
| 8,155,421 | B2 | 4/2012 | Ren et al. |
| 8,170,320 | B2 | 5/2012 | Smith et al. |
| 8,175,219 | B2 | 5/2012 | Defreitas et al. |
| 8,275,090 | B2 | 9/2012 | Ren |
| 8,285,020 | B2 | 10/2012 | Gkanatsios et al. |
| 8,416,915 | B2 | 4/2013 | Jing et al. |
| 8,452,379 | B2 | 5/2013 | DeFreitas et al. |
| 8,457,282 | B2 | 6/2013 | Baorui et al. |
| 8,515,005 | B2 | 8/2013 | Ren et al. |
| 8,559,595 | B2 | 10/2013 | Defreitas et al. |
| 8,565,372 | B2 | 10/2013 | Stein et al. |
| 8,565,374 | B2 | 10/2013 | DeFreitas et al. |
| 8,565,860 | B2 | 10/2013 | Kimchy |
| 8,571,289 | B2 | 10/2013 | Ruth et al. |
| 8,712,127 | B2 | 4/2014 | Ren et al. |
| 8,767,911 | B2 | 7/2014 | Ren et al. |
| 8,787,522 | B2 | 7/2014 | Smith et al. |
| 8,824,752 | B1 | 9/2014 | Fonte |
| 8,831,171 | B2 | 9/2014 | Jing et al. |
| 8,853,635 | B2 | 10/2014 | O'Connor |
| 8,873,716 | B2 | 10/2014 | Ren et al. |
| 9,020,579 | B2 | 4/2015 | Smith |
| 9,042,612 | B2 | 5/2015 | Gkanatsios et al. |
| 9,066,706 | B2 | 6/2015 | Defreitas et al. |
| 9,226,721 | B2 | 1/2016 | Ren et al. |
| 9,235,888 | B2 | 1/2016 | Jerebko |
| 9,460,508 | B2 | 10/2016 | Gkanatsios et al. |
| 9,498,175 | B2 | 11/2016 | Stein et al. |
| 9,498,180 | B2 | 11/2016 | Ren |
| 9,502,148 | B2 | 11/2016 | Ren |
| 9,549,709 | B2 | 1/2017 | DeFreitas et al. |
| 9,668,711 | B2 | 6/2017 | Smith |
| 9,808,214 | B2 | 11/2017 | Smith |
| 9,851,888 | B2 | 12/2017 | Gkanatsios et al. |
| 9,895,115 | B2 | 2/2018 | Ren |
| 10,098,601 | B2 | 10/2018 | Smith |
| 10,108,329 | B2 | 10/2018 | Gkanatsios et al. |
| 10,194,875 | B2 | 2/2019 | DeFreitas et al. |
| 10,296,199 | B2 | 5/2019 | Gkanatsios |
| 10,357,211 | B2 | 7/2019 | Smith et al. |
| 10,413,255 | B2 | 9/2019 | Stein |
| 10,452,252 | B2 | 10/2019 | Gkanatsios et al. |
| 10,561,387 | B2 | 2/2020 | Smith |
| 10,575,804 | B2 | 3/2020 | Smith et al. |
| 10,638,994 | B2 | 5/2020 | DeFreitas |
| 10,719,223 | B2 | 7/2020 | Gkanatsios |
| 10,792,003 | B2 | 10/2020 | Smith |
| 10,881,359 | B2 | 1/2021 | Williams |
| 10,905,385 | B2 | 2/2021 | DeFreitas |
| 10,959,694 | B2 | 3/2021 | Jing et al. |
| 11,076,820 | B2 | 8/2021 | Smith |
| 11,090,017 | B2 | 8/2021 | Zhang |
| 11,096,644 | B2 | 8/2021 | DeFreitas |
| 11,191,502 | B2 | 12/2021 | Smith |
| 11,419,569 | B2 | 8/2022 | Wong |
| 11,478,206 | B2 | 10/2022 | Smith |
| 11,672,500 | B2 | 6/2023 | Wong |
| 12,053,319 | B2 | 8/2024 | Wong |
| 12,159,419 | B2 | 12/2024 | Ren |
| 2001/0038681 | A1 | 11/2001 | Stanton et al. |
| 2002/0012450 | A1 | 1/2002 | Tsujii |
| 2002/0048343 | A1 | 4/2002 | Launay et al. |
| 2002/0050986 | A1 | 5/2002 | Inouc et al. |
| 2002/0070970 | A1 | 6/2002 | Wood et al. |
| 2002/0075997 | A1 | 6/2002 | Unger et al. |
| 2002/0090055 | A1 | 7/2002 | Zur et al. |
| 2002/0094062 | A1 | 7/2002 | Dolazza |
| 2002/0122533 | A1 | 9/2002 | Marie et al. |
| 2002/0126798 | A1 | 9/2002 | Harris |
| 2003/0007598 | A1 | 1/2003 | Wang et al. |
| 2003/0010923 | A1 | 1/2003 | Zur |
| 2003/0018272 | A1 | 1/2003 | Treado et al. |
| 2003/0026386 | A1 | 2/2003 | Tang et al. |
| 2003/0058989 | A1 | 3/2003 | Rotondo |
| 2003/0072409 | A1 | 4/2003 | Kaufhold et al. |
| 2003/0072417 | A1 | 4/2003 | Kaufhold et al. |
| 2003/0073895 | A1 | 4/2003 | Nields et al. |
| 2003/0095624 | A1 | 5/2003 | Eberhard et al. |
| 2003/0095697 | A1 | 5/2003 | Wood et al. |
| 2003/0097055 | A1 | 5/2003 | Yanof et al. |
| 2003/0149364 | A1 | 8/2003 | Kapur |
| 2003/0169847 | A1 | 9/2003 | Karellas et al. |
| 2003/0194049 | A1 | 10/2003 | Claus et al. |
| 2003/0194050 | A1 | 10/2003 | Eberhard |

(56) References Cited

U.S. PATENT DOCUMENTS

2003/0194051 A1 10/2003 Wang et al.
2003/0194121 A1 10/2003 Eberhard et al.
2003/0210254 A1 11/2003 Doan et al.
2003/0212327 A1 11/2003 Wang et al.
2003/0215120 A1 11/2003 Uppaluri et al.
2004/0008809 A1 1/2004 Webber
2004/0052328 A1 3/2004 Sabol
2004/0066882 A1 4/2004 Eberhard et al.
2004/0066884 A1 4/2004 Hermann Claus
2004/0066904 A1 4/2004 Eberhard et al.
2004/0070582 A1 4/2004 Smith et al.
2004/0081273 A1 4/2004 Ning
2004/0094167 A1 5/2004 Brady et al.
2004/0101095 A1 5/2004 Jing et al.
2004/0109529 A1 6/2004 Eberhard et al.
2004/0146221 A1 7/2004 Siegel et al.
2004/0170561 A1 9/2004 Salb et al.
2004/0171986 A1 9/2004 Tremaglio, Jr. et al.
2004/0190682 A1 9/2004 Deuringer
2004/0213378 A1 10/2004 Zhou et al.
2004/0247081 A1 12/2004 Halsmer
2004/0264627 A1 12/2004 Besson
2004/0267157 A1 12/2004 Miller et al.
2005/0025278 A1 2/2005 Hagiwara
2005/0049521 A1 3/2005 Miller et al.
2005/0063509 A1 3/2005 DeFreitas et al.
2005/0078797 A1 4/2005 Danielsson et al.
2005/0084060 A1 4/2005 Seppi et al.
2005/0084073 A1 4/2005 Seppi
2005/0089205 A1 4/2005 Kapur
2005/0105679 A1 5/2005 Wu et al.
2005/0113681 A1 5/2005 DeFreitas et al.
2005/0113715 A1 5/2005 Schwindt et al.
2005/0117694 A1 6/2005 Francke
2005/0129172 A1 6/2005 Mertelmeier
2005/0133706 A1 6/2005 Eberhard
2005/0135555 A1 6/2005 Claus et al.
2005/0135664 A1 6/2005 Kaufhold et al.
2005/0152590 A1 7/2005 Thieret et al.
2005/0226375 A1 10/2005 Eberhard et al.
2005/0248347 A1 11/2005 Damadian
2005/0267157 A1 12/2005 White et al.
2006/0004278 A1 1/2006 Giger et al.
2006/0030784 A1 2/2006 Miller et al.
2006/0034426 A1 2/2006 Freudenberger
2006/0074288 A1 4/2006 Kelly
2006/0098855 A1 5/2006 Gkanatsios et al.
2006/0109951 A1 5/2006 Popescu
2006/0126780 A1 6/2006 Rotondo
2006/0129062 A1 6/2006 Nicoson et al.
2006/0146982 A1 7/2006 Kaipio et al.
2006/0155209 A1 7/2006 Miller et al.
2006/0210016 A1 9/2006 Francke
2006/0262898 A1 11/2006 Partain
2006/0269041 A1 11/2006 Mertelmeier
2006/0291618 A1 12/2006 Eberhard et al.
2007/0030949 A1 2/2007 Jing et al.
2007/0036265 A1 2/2007 Jing et al.
2007/0076844 A1 4/2007 Defreitas et al.
2007/0078335 A1 4/2007 Horn
2007/0133738 A1 6/2007 Zimmermann
2007/0140419 A1 6/2007 Souchay
2007/0183564 A1 8/2007 Li et al.
2007/0217573 A1 9/2007 Berhardt
2007/0223651 A1 9/2007 Wagenaar et al.
2007/0225600 A1 9/2007 Weibrecht et al.
2007/0242797 A1 10/2007 Stewart et al.
2007/0242800 A1 10/2007 Jing et al.
2007/0263765 A1 11/2007 Wu
2007/0280412 A1 12/2007 DeFreitas
2008/0019581 A1 1/2008 Gkanatsios et al.
2008/0045833 A1 2/2008 Defreitas et al.
2008/0056436 A1 3/2008 Pack
2008/0056441 A1 3/2008 Souchay
2008/0089471 A1 4/2008 Kobayashi
2008/0101536 A1 5/2008 Sendai
2008/0101537 A1 5/2008 Sendai
2008/0112534 A1 5/2008 Defreitas
2008/0118023 A1 5/2008 Besson
2008/0130979 A1 6/2008 Ren
2008/0212861 A1 9/2008 Durgan et al.
2008/0267484 A1 10/2008 Chen
2008/0285712 A1 11/2008 Kopans
2008/0317196 A1 12/2008 Imai
2009/0003519 A1 1/2009 Defreitas et al.
2009/0010384 A1 1/2009 Jing et al.
2009/0080594 A1 3/2009 Brooks et al.
2009/0080602 A1 3/2009 Brooks et al.
2009/0123052 A1 5/2009 Ruth
2009/0135995 A1 5/2009 Eberhard et al.
2009/0135997 A1 5/2009 Defreitas et al.
2009/0141859 A1 6/2009 Gkanatsios et al.
2009/0154787 A1 6/2009 Bertram et al.
2009/0175408 A1 7/2009 Goodsitt et al.
2009/0213987 A1 8/2009 Stein et al.
2009/0237924 A1 9/2009 Ladewig
2009/0238424 A1 9/2009 Arakita et al.
2009/0262887 A1 10/2009 Lordache
2009/0268865 A1 10/2009 Ren et al.
2009/0296882 A1 12/2009 Gkanatsios
2009/0304147 A1* 12/2009 Jing .................... A61B 6/4429
382/131
2010/0020937 A1 1/2010 Hautmann
2010/0020938 A1 1/2010 Koch
2010/0034450 A1 2/2010 Mertelmeier
2010/0054400 A1 3/2010 Ren
2010/0080343 A1 4/2010 Kalender et al.
2010/0086188 A1 4/2010 Ruth
2010/0091940 A1 4/2010 Ludwig et al.
2010/0150306 A1 6/2010 Defreitas et al.
2010/0150417 A1 6/2010 Kshirsagar
2010/0177866 A1 7/2010 Shibuya
2010/0189227 A1 7/2010 Mannar
2010/0195882 A1 8/2010 Ren
2010/0195885 A1 8/2010 Ma
2010/0208037 A1 8/2010 Sendai
2010/0226475 A1 9/2010 Smith
2010/0290585 A1 11/2010 Eliasson
2010/0303202 A1 12/2010 Ren
2010/0313196 A1 12/2010 De Atley
2010/0329514 A1 12/2010 Mundry
2011/0026667 A1 2/2011 Poorter
2011/0069809 A1 3/2011 Defreitas et al.
2011/0178389 A1 7/2011 Kumar et al.
2011/0188624 A1 8/2011 Ren
2011/0234630 A1 9/2011 Batman et al.
2011/0257919 A1 10/2011 Reiner
2011/0268246 A1 11/2011 Dafni
2012/0033868 A1 2/2012 Ren
2012/0051502 A1 3/2012 Ohta et al.
2012/0112088 A1 5/2012 Abraham
2012/0114095 A1 5/2012 Smith et al.
2012/0189175 A1 7/2012 Highnam
2012/0236987 A1 9/2012 Ruimi
2012/0238870 A1 9/2012 Smith et al.
2013/0028374 A1 1/2013 Gkanatsios et al.
2013/0211261 A1 8/2013 Wang
2013/0259193 A1 10/2013 Packard et al.
2013/0272493 A1 10/2013 Otokuni
2013/0272494 A1 10/2013 DeFreitas et al.
2014/0044230 A1 2/2014 Stein et al.
2014/0044231 A1 2/2014 Defreitas et al.
2014/0086471 A1 3/2014 Ruth et al.
2014/0098935 A1 4/2014 Defreitas et al.
2014/0232752 A1 8/2014 Ren et al.
2014/0314198 A1 10/2014 Ren et al.
2014/0321607 A1 10/2014 Smith
2014/0328458 A1 11/2014 Erhard
2014/0376690 A1 12/2014 Jing et al.
2015/0010219 A1 1/2015 Behiels
2015/0049859 A1 2/2015 DeFreitas et al.
2015/0160848 A1 6/2015 Gkanatsios et al.
2015/0310611 A1 10/2015 Gkanatsios et al.
2015/0327826 A1 11/2015 Smith et al.

(56) References Cited

U.S. PATENT DOCUMENTS

| | | | |
|---|---|---|---|
| 2015/0332485 | A1 | 11/2015 | Klausz |
| 2015/0342549 | A1 | 12/2015 | Kwon |
| 2016/0066875 | A1 | 3/2016 | Jacob et al. |
| 2016/0095563 | A1 | 4/2016 | Fukuda et al. |
| 2016/0106383 | A1 | 4/2016 | Ren et al. |
| 2016/0133033 | A1 | 5/2016 | Highnam |
| 2016/0189376 | A1 | 6/2016 | Bernard |
| 2016/0209995 | A1 | 7/2016 | Jeon |
| 2016/0220207 | A1 | 8/2016 | Jouhikainen |
| 2016/0256125 | A1 | 9/2016 | Smith |
| 2016/0270742 | A9 | 9/2016 | Stein et al. |
| 2016/0302746 | A1 | 10/2016 | Erhard |
| 2016/0331339 | A1 | 11/2016 | Guo |
| 2017/0024113 | A1 | 1/2017 | Gkanatsios et al. |
| 2017/0032546 | A1 | 2/2017 | Westerhoff |
| 2017/0071562 | A1 | 3/2017 | Suzuki |
| 2017/0086765 | A1 | 3/2017 | Smith et al. |
| 2017/0128028 | A1 | 5/2017 | DeFreitas et al. |
| 2017/0132792 | A1 | 5/2017 | Jerebko |
| 2017/0135650 | A1 | 5/2017 | Stein et al. |
| 2017/0316588 | A1 | 11/2017 | Homann |
| 2017/0319167 | A1 | 11/2017 | Goto |
| 2017/0367674 | A1 | 12/2017 | Arai et al. |
| 2018/0035963 | A1 | 2/2018 | Smith et al. |
| 2018/0046875 | A1 | 2/2018 | Caluser |
| 2018/0122067 | A1 | 5/2018 | Reicher |
| 2018/0130201 | A1 | 5/2018 | Bernard |
| 2018/0177476 | A1 | 6/2018 | Jing et al. |
| 2018/0188937 | A1 | 7/2018 | Gkanatsios et al. |
| 2018/0289347 | A1 | 10/2018 | DeFreitas et al. |
| 2018/0344276 | A1 | 12/2018 | DeFreitas et al. |
| 2019/0059830 | A1 | 2/2019 | Williams |
| 2019/0059841 | A1 | 2/2019 | Palma et al. |
| 2019/0095087 | A1 | 3/2019 | Gkanatsios et al. |
| 2019/0110769 | A1 | 4/2019 | Smith |
| 2019/0200942 | A1 | 7/2019 | DeFreitas |
| 2019/0287241 | A1 | 9/2019 | Hill |
| 2019/0290221 | A1 | 9/2019 | Smith et al. |
| 2019/0336794 | A1 | 11/2019 | Li |
| 2019/0388051 | A1 | 12/2019 | Morita |
| 2020/0012417 | A1 | 1/2020 | Gkanatsios |
| 2020/0029927 | A1 | 1/2020 | Wilson |
| 2020/0085393 | A1 | 3/2020 | Zhang |
| 2020/0222023 | A1 | 7/2020 | Wong |
| 2020/0348835 | A1 | 11/2020 | Gkanatsios |
| 2020/0352531 | A1 | 11/2020 | Smith |
| 2020/0372693 | A1 | 11/2020 | Kobayashi |
| 2021/0097677 | A1 | 4/2021 | Highnam |
| 2021/0113168 | A1 | 4/2021 | Smith |
| 2021/0128087 | A1 | 5/2021 | DeFreitas |
| 2021/0298700 | A1 | 9/2021 | Williams |
| 2022/0071582 | A1 | 3/2022 | DeFreitas |
| 2022/0133252 | A1 | 5/2022 | Smith |
| 2022/0343513 | A1 | 10/2022 | Ren |
| 2022/0361831 | A1 | 11/2022 | Hartig |
| 2022/0378389 | A1 | 12/2022 | Wong |
| 2023/0000455 | A1 | 1/2023 | Wong |
| 2023/0121010 | A1 | 4/2023 | Smith |
| 2025/0191200 | A1 | 6/2025 | Ren |
| 2025/0331795 | A1 | 10/2025 | Smith |

FOREIGN PATENT DOCUMENTS

| | | | |
|---|---|---|---|
| CN | 101842052 | A | 9/2010 |
| CN | 102222594 | | 10/2011 |
| CN | 105286904 | | 2/2016 |
| CN | 103179906 | B | 4/2016 |
| CN | 105637562 | | 6/2016 |
| CN | 109419526 | | 3/2019 |
| DE | 102004051401 | | 5/2006 |
| DE | 102004051820 | | 5/2006 |
| DE | 102010027871 | | 10/2011 |
| EP | 0543801 | | 5/1988 |
| EP | 0775467 | | 5/1997 |
| EP | 0982001 | | 3/2000 |
| EP | 1028451 | | 8/2000 |
| EP | 1398721 | | 3/2004 |
| EP | 1428473 | | 6/2004 |
| EP | 1759637 | | 3/2007 |
| EP | 2366172 | | 9/2011 |
| EP | 1569556 | | 4/2012 |
| EP | 2732764 | | 5/2014 |
| EP | 2602743 | | 11/2014 |
| EP | 2819145 | | 12/2014 |
| EP | 3143935 | | 3/2017 |
| JP | 53151381 | U | 11/1978 |
| JP | 10-165403 | | 6/1998 |
| JP | 2001-346786 | | 12/2001 |
| JP | 2002-219124 | | 8/2002 |
| JP | 2008-093135 | | 4/2006 |
| JP | 2006-136741 | | 6/2006 |
| JP | 2006-231054 | | 9/2006 |
| JP | 2007-50264 | | 3/2007 |
| JP | 2007-521911 | | 8/2007 |
| JP | 2007-229269 | | 9/2007 |
| JP | 2008-67933 | | 3/2008 |
| JP | 2008-086471 | | 4/2008 |
| JP | 2009-500048 | | 1/2009 |
| JP | 2011-072667 | | 4/2011 |
| JP | 2011-250842 | | 12/2011 |
| JP | 2012-035068 | | 2/2012 |
| JP | 2012-509714 | | 4/2012 |
| JP | 2012-511988 | | 5/2012 |
| JP | 2012-157551 | | 8/2012 |
| JP | 2015-530706 | | 10/2015 |
| JP | 2019-103944 | | 6/2019 |
| KR | 10-2010-0114090 | | 10/2010 |
| WO | 90/05485 | | 5/1990 |
| WO | 98/03115 | | 1/1998 |
| WO | 98/16903 | | 4/1998 |
| WO | 00/51484 | | 9/2000 |
| WO | 01/22363 | | 3/2001 |
| WO | 03/020114 | | 3/2003 |
| WO | 03/037046 | | 5/2003 |
| WO | 2003/057564 | | 7/2003 |
| WO | 03/073939 | | 9/2003 |
| WO | 2004/043535 | | 5/2004 |
| WO | 2005/051197 | | 6/2005 |
| WO | 2005/071601 | | 8/2005 |
| WO | 2005/110230 | | 11/2005 |
| WO | 2005/112767 | | 12/2005 |
| WO | 2006/055830 | | 5/2006 |
| WO | 2006/058160 | | 6/2006 |
| WO | 2007/129244 | | 11/2007 |
| WO | 2008/072144 | | 6/2008 |
| WO | 2009/104156 | | 8/2009 |
| WO | 2009/122328 | | 10/2009 |
| WO | 2009/136349 | | 11/2009 |
| WO | 2010/061003 | | 6/2010 |
| WO | 2010/062291 | | 6/2010 |
| WO | 2010/070554 | | 6/2010 |
| WO | 2011/058730 | | 5/2011 |
| WO | 2012/048000 | | 4/2012 |
| WO | 2013/184213 | | 12/2013 |
| WO | 2014/176445 | | 10/2014 |
| WO | 2015/054518 | | 4/2015 |
| WO | 2015/175728 | | 11/2015 |
| WO | 2014/203531 | | 2/2017 |
| WO | 2018/170265 | | 9/2018 |

OTHER PUBLICATIONS

PCT International Search Report and Written Opinion in Application PCT/US2023/069518, mailed Oct. 23, 2023, 15 pages.
"Essentials for life: Senographe Essential Full-Field Digital Mammography system", GE Health-care Brochure, MM-0132-05.06-EN-US, 2006, 12 pgs.
"Filtered Back Projection," (NYGREN) published May 8, 2007; URL:http://web.archive.org/web/19991010131715/http://www.owlnet.rice.edu/-.about.e1ec539/Projects97/cult/node2.html., 2 pgs.
"Lorad Selenia" Document B-BI-SEO US/Intl (May 2006) copyright Hologic 2006, 12 pgs.

(56) References Cited

OTHER PUBLICATIONS

ACRIN website, located at https://www.acrin.org/PATIENTS/ABOUTIMAGINGEXAMSANDAGENTS/ABOUTMAMMOGRAPHYANDTOMOSYNTHESIS.aspx, "About Mammography and Tomosynthesis", obtained online on Dec. 8, 2015, 5 pgs.
American College of Radiology website, located at http://www.acr.org/FAQs/DBT-FAQ, "Digital Breast Tomosynthesis FAQ For Insurers", obtained online on Dec. 8, 2015, 2 pages.
Aslund, Magnus, "Digital Mammography with a Photon Counting Detector in a Scanned Multislit Geometry", Doctoral Thesis, Dept of Physics, Royal Institute of Technology, Stockholm, Sweden, Apr. 2007, 51 pages.
Carlborn, et al., "Computer-assisted registration, segmentation, and 3D reconstruction from images of neuronal tissue sections", IEEE Transactions on Medical Imaging, vol. 13, No. 2, Jun. 1994, pp. 351-362.
Chan, Heang-Ping et al., "ROC study of the effect of stereoscopic imaging on assessment of breast lesions", Medical Physics, vol. 32, No. 4, Apr. 2005, 7 pgs.
Cole, Elodia, et al., "The Effects of Gray Scale Image Processing on Digital Mammography Interpretation Performance", Academic Radiology, vol. 12, No. 5, pp. 585-595, May 2005.
Digital Clinical Reports, Tomosynthesis, GE Brochure 98-5493, Nov. 1998, 8 pgs.
Dobbins, James T., "Digital x-ray tomosynthesis: current state of the art and clinical potential," Physics in Medicine and Biology, Taylor and Francis LTD, London GB, vol. 48, No. 19, Oct. 7, 2003, 42 pages.
Grant, David G., "Tomosynthesis: a three-dimensional imaging technique", IEEE Trans. Biomed. Engineering, vol. BME-19, #1, Jan. 1972, pp. 20-28.
Kachelriess, Marc et al., "Flying Focal Spot (FFS) in Cone-Beam CT", 2004 IEEE Nuclear Science Symposium Conference Record, Oct. 16-22, 2004, Rome Italy, vol. 6, pp. 3759-3763.
Kita et al., "Correspondence between different view breast X-rays using simulation of breast deformation", Proceedings 1998 IEE Computer Society Conference on Computer Vision and Pattern Recognition, Santa Barbara, CA, Jun. 23-25, 1998, pp. 700-707.
Kopans, Daniel B., "Breast Imaging", Chapter 26: Future Advances in Breast Imaging, 2nd Edition, Lippincott-Raven Publishers, Philadelphia, 1998, 37 pages.
Mammographic Accreditation Phantom, http://www.cirsinc.com/pdfs/015cp.pdf. (2006), 2 pgs.
Niklason et al., "Digital breast tomosynthesis: potentially a new method for breast cancer screening", In Digital Mammography, 1998, 6 pages.
Niklason, Loren T. et al., "Digital Tomosynthesis in Breast Imaging", Radiology, Nov. 1997, vol. 205, No. 2, pp. 399-406.
Pediconi, Federica et al., "Color-coded automated signal intensity-curve for detection and characterization of breast lesions: Preliminary evaluation of a new software for MR-based breast imaging", International Congress Series 1281 (2005) 1081-1086.
Pisano, Etta D., "Digital Mammography", Radiology, vol. 234, No. 2, Feb. 2005, pp. 353-362.
Ren, B. et al., "Automatic patient motion detection in digital breast tomosynthesis", Medical Imaging 2011: Physics of Medical Imaging, SPIE, 7961(1): 1-12 (Mar. 2011).
Senographe 700 & 800T (GE); 2-page download on Jun. 22, 2006 from www.gehealthcare.com/inen/rad/whe/products/mswh800t.html.; Figures 1-7 on 4 sheets re lateral shift compression paddle, 2 pgs.
Smith, A., "Fundamentals of Breast Tomosynthesis", White Paper, Hologic Inc., WP-00007, Jun. 2008, 8 pgs.
Smith, Andrew, PhD, "Full Field Breast Tomosynthesis", Hologic White Paper, Oct. 2004, 6 pgs.
Spetsieris et al., "Interactive visualization of coregistered tomographic images", Biomedical Visualization, 1995, IEEE Computer Soc., 1995, Eds: Loew and Gershon, pp. 58-63.
Thurfjell, "Mammography screening: one versus two views and independent double reading", Acta Radiologica 35, No. 4, 1994, pp. 345-350.
Wheeler F. W., et al. "Micro-Calcification Detection in Digital Tomosynthesis Mammography", Proceedings of SPIE, Conf-Physics of Semiconductor Devices, Dec. 11, 2001 to Dec. 15, 2001, Delhi, SPIE, US, vol. 6144, Feb. 13, 2006, 12 pgs.
Wu, Tao, et al. "Tomographic Mammography Using a Limited Number of Low-Dose Cone-Beam Projection Images" Medical Physics, AIP, Melville, NY, vol. 30, No. 3, Mar. 1, 2003, p. 365-380.
Zhao, Bo et al., "Three-dimensional linear system analysis for breast tomosynthesis", Medical Physics, vol. 35, No. 12, Nov. 6, 2008, pp. 5219-5232.

* cited by examiner

WIDE ANGLE AUTOMATIC EXPOSURE CONTROL IN TOMOSYNTHESIS

CROSS-REFERENCE TO RELATED APPLICATION

This application is a National Stage Application of PCT/US2023/069518, filed on Jun. 30, 2023, which claims priority to and the benefit of U.S. Provisional Application No. 63/358,350, filed on Jul. 5, 2022, the entire disclosures of which are incorporated herein by reference in their entireties. To the extent appropriate, a claim of priority is made to each of the above disclosed applications.

BACKGROUND

Breast cancer and other breast lesions continue to be a significant threat to women's health. X-ray mammography and tomosynthesis are the most widely used tools for early detection, screening and diagnosis. Tomosynthesis is a technique that allows physicians to view multiple images of the breast rather than a single image available from a conventional mammogram.

For example, conventional mammography provides physicians with a single two-dimensional (2D) image to evaluate the breast. However, this can be limiting due to the overlapping layers of tissue, which can produce unclear results, false positives, or can lead the physician to miss cancerous growth. By contrast, tomosynthesis generates multiple x-ray images of the breast, as the x-ray source moves relative to the breast. The x-ray images are then processed into a stack of 2D images that represent an entire volume of the breast that allows physicians to better evaluate the patient's breast.

SUMMARY

Examples of the disclosure are directed to automatic exposure control methods and systems for wide-angle tomosynthesis.

In a first example, a method of performing an automatic exposure control (AEC) operation using a tomosynthesis system is disclosed. The method comprises: acquiring a scout image of a patient's breast at a first projection angle by emitting a scout x-ray dosage towards the patient's breast with the tomosynthesis system, the scout image including a plurality of pixels, wherein each of the plurality of pixels is associated with a detector count value from among a plurality of detector count values: identifying a first region on the scout image as corresponding to a densest portion of the patient's breast; calculating an average detector count value by averaging the one or more detector count values corresponding to the one or more pixels within the first region; identifying a second region on a first reference image associated with the first projection angle, wherein the second region corresponds to a location on the first reference image that matches a location of the first region on the scout image: obtaining one or more reference detector count values associated with one or more reference pixels within the second region of the first reference image; calculating an average reference detector count value by averaging the one or more reference detector count values; based on a ratio between the average reference detector count value and the average detector count value, calculating an AEC calibrated dosage to use in a tomosynthesis scan; and setting a radiation dosage for a tomosynthesis sweep at a plurality of projection angles on the patient's breast to the AEC calibrated dosage.

In a second example, a tomosynthesis system for performing an automatic exposure control (AEC) operation is disclosed. The system comprises: a processor; memory including instructions that when executed by the processor cause the processor to: acquire a scout image of a patient's breast at a first projection angle by emitting a scout x-ray dosage towards the patient's breast with the tomosynthesis system, the scout image including a plurality of pixels, wherein each of the plurality of pixels is associated with a detector count value from among a plurality of detector count values; identify a first region on the scout image as corresponding to a densest portion of the patient's breast; calculate an average detector count value by averaging the one or more detector count values corresponding to the one or more pixels within the first region; identify a second region on a first reference image associated with the first projection angle, wherein the second region corresponds to a location on the first reference image that matches a location of the first region on the scout image: obtain one or more reference detector count values associated with one or more reference pixels within the second region of the first reference image: calculate an average reference detector count value by averaging the one or more reference detector count values; based on a ratio between the average reference detector count value and the average detector count value, calculate an AEC calibrated dosage to use in a tomosynthesis scan; and set a radiation dosage for a tomosynthesis sweep at a plurality of projection angles on the patient's breast to the AEC calibrated dosage.

In a third example, a method of performing a calibration operation associated with an automatic exposure control (AEC) operation using a tomosynthesis system is disclosed. The method comprises: acquiring a plurality of reference images of a phantom at a plurality of projection angles, wherein each of the plurality of reference images include a plurality of reference image pixels: generating a plurality of reference image detector count maps corresponding to each of the plurality of reference images by compiling a plurality of reference image pixels and corresponding reference image detector count values associated for each of the plurality of reference images: storing the plurality of reference image detector count maps: acquiring a scout image of a patient's breast at the first projection angle by emitting a scout x-ray dosage towards the patient's breast with the tomosynthesis system, the scout image including a plurality of pixels, wherein each of the plurality of pixels is associated with a detector count value from among a plurality of detector count values; identifying a first region on the scout image as corresponding to a densest portion of the patient's breast; calculating an average detector count value by averaging the one or more detector count values corresponding to the one or more pixels within the first region; identifying a second region on a first reference image associated with a first projection angle, wherein the second region corresponds to a location on the first reference image that matches a location of the first region on the scout image and the first projection angle is one of the plurality of projection angles and the first reference image is one of the plurality of reference images: obtaining one or more reference detector count values associated with one or more reference pixels within the second region of the first reference image:

calculating an average reference detector count value by averaging the one or more reference detector count values; based on a ratio between the average reference detector count value and the average detector count value, calculating an AEC calibrated dosage to use in a tomosynthesis scan; and setting a radiation dosage for a tomosynthesis sweep at a plurality of projection angles on the patient's breast to the AEC calibrated dosage.

BRIEF DESCRIPTION OF DRAWINGS

The following drawings are illustrative of particular examples of the present disclosure and therefore do not limit the scope of the present disclosure. The drawings are not to scale and are intended for use in conjunction with the explanations in the following detailed description. Examples of the present disclosure will hereinafter be described in conjunction with the appended drawings, wherein like numerals denote like elements.

DETAILED DESCRIPTION

Figure 1A:
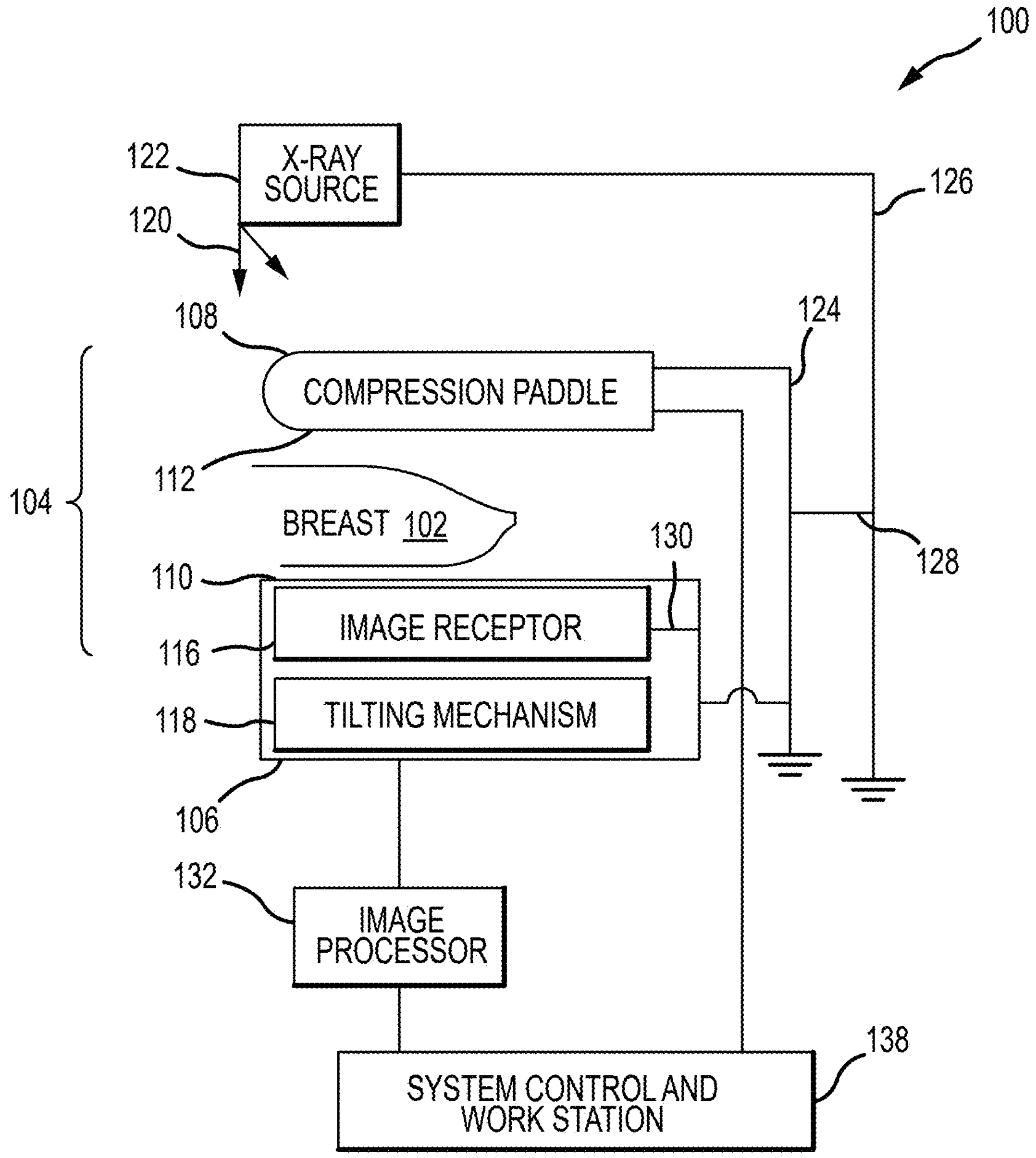
FIG. 1A is a schematic view of an exemplary imaging system.

Various examples will be described in detail with reference to the drawings, wherein like reference numerals represent like parts and assemblies throughout the several views. Reference to various examples does not limit the scope of the claims attached hereto. Additionally, any examples set forth in this specification are not intended to be limiting and merely set forth some of the many possible examples for the appended claims.

Digital tomosynthesis is a process in which several two-dimensional projection views are acquired at different projection angles. The total range of angles over which x-ray images are obtained is usually about +/−7.5 degrees. Each of the images is acquired using a lower x-ray dose compared to a conventional mammogram. The acquired two-dimensional projection views are reconstructed into tomosynthesis slice views that can be along any desired plane in the breast and can represent any thickness of breast tissue. Thus, the combined reconstructed tomosynthesis image set represents the entire volume of the breast, in a stack of two-dimensional images. For tomosynthesis, the breast is immobilized or compressed to the same or lesser extent than in conventional mammography.

Typically, tomosynthesis systems may use an automatic exposure control (AEC) system and method to automatically control the quantity of radiation delivered to a patient's breast. The AEC system may automatically terminate the exposure when a desired quantity of radiation has been delivered. The desired quantity of radiation is based on balancing the need to minimize the amount of radiation exposure for the patient with generating adequately exposed images.

The AEC system may operate by controlling one or more technique factors in order to obtain the desired quantity of radiation, including the kilovoltage peak (kVp), which is the difference in potential applied across the x-ray cathode and x-ray anode tube and milliampere-seconds (mAs), which is a measure of current from the x-ray cathode to x-ray anode applied over a set amount of time via an x-ray tube. The combination of the kVp and mAs values directly influence the radiation dose delivered to the patient breast and image quality of mammogram. In some examples, an operator of the tomosynthesis system may select the kVp value based on thickness of the patient's breast and the mAs value may be varied by the AEC system to achieve the desired radiation levels. In other examples, the AEC system may select both kVp and mAs values as well.

Generally, the AEC system may initially deliver a short, low dose x-ray pulse or emission to the patient's breast. The image receptor's resulting scout image is read by a computer process to determine the breast area of the greatest radiodensity. Based on the detector values at the breast area of the greatest radiodensity within the scout image, the AEC system may calculate the correct final AEC dosage, including kVp and mAs values, to generate an adequately exposed final image.

However, AEC for wide-angle tomosynthesis has several challenges that are not seen in narrow-angle tomosyntheses. Here, "wide-angle tomosynthesis" may be defined as ranges greater than about +/−15 degrees. In a typical tomosynthesis system, the scout exposure and image are acquired at a zero degree angle to the breast. In wide-angle tomosynthesis, the scout exposure may take place at large incident angles to the breast that is far away from the zero-degree normal direction to the breast. For example, the scout exposure angle may range anywhere between +/−30 degrees or even +/−60 degrees. The scout exposure may typically be acquired any angle within the range of angles at which the x-ray source and the tomosynthesis equipment is positioned at after the previous use of the equipment. In other words, the tomosynthesis equipment need not be re-set or re-aligned to a certain angle, such as 0 degrees, in order to perform the scout exposure. This allows for using the tomosynthesis equipment without wasting time on resetting the equipment to a 0 degree angle between use. Rather the disclosed system and method describe accurately acquiring images when the incident angle of the scout exposure is anywhere within the range of angles by adequately taking the incident angle into consideration. At large incident angles, the x-ray path length through the breast is much longer than breast compression thickness. Therefore, to accurately calculate AEC dosage, the AEC system needs to take into consideration parameters such as angle of emission and "heel effect". Heel effect is caused due to the drop in x-ray intensity along the direction from the chest wall to the nipple.

For example, the angle and heel effects influence the accuracy of the calculated AEC dosage because the detector count values at the detector center from the scout exposure decreases as AEC tube angle increases. In other words, the larger the projection angle, the smaller the detector count from scout exposure of the same x-ray dosage. In addition, the detector pixels at the far side of detector to the chest wall tends to see a lower count than those pixels at the chest wall side of detector. Further, as the projection angle varies, the center location of the breast as projected on the detector shifts. Since the densest portion of the breast is typically selected for dosage calculations from the center location of the breast, the shifts in center location must be accounted for in order to accurately calculate the AEC dosage.

To accurately calculate the radiation dosage that produces adequately exposed images that meet image quality thresholds from the wide-angle tomosynthesis process, the present disclosure generates reference detector count maps at each of the projection angles. For example, one or more wide-angle tomosynthesis scans with a high x-ray dosage may be performed on a uniform phantom at one or more projection angles to generate a reference detector count map for each of the one or more discrete angles. A look up table with scale factors may also be used to also generate reference detector count maps for different thicknesses of breasts. Curve fitting may be applied to the reference detector count map to derive the detector count values at intervening projection angles. The reference detector count maps associated with each of the plurality of projection angles may be stored and used in calculating the AEC x-ray dosage needed to acquire the x-ray images during tomosynthesis scan.

The process of calculating the x-ray dosage starts with acquiring a scout image of a patient's breast at a first projection angle using a scout dosage. Once the scout image is acquired, the densest portions of the patient's breast is identified within the scout image and an average detector count value associated with the identified densest portion of the patient's breast is calculated. The reference image and corresponding reference detector count map associated with the first projection angle is then retrieved. A second region corresponding to the location of the first region on the scout image is then identified within the reference image. The reference detector count map is used to determine the reference detector count values associated with the second region on the reference image and an average reference detector count value associated with the second region is calculated. The reference x-ray dosage value and the ratio of the average reference detector count value to the average detector count value can be used to calculate the x-ray dosage needed for the tomosynthesis scan.

Figure 1B:
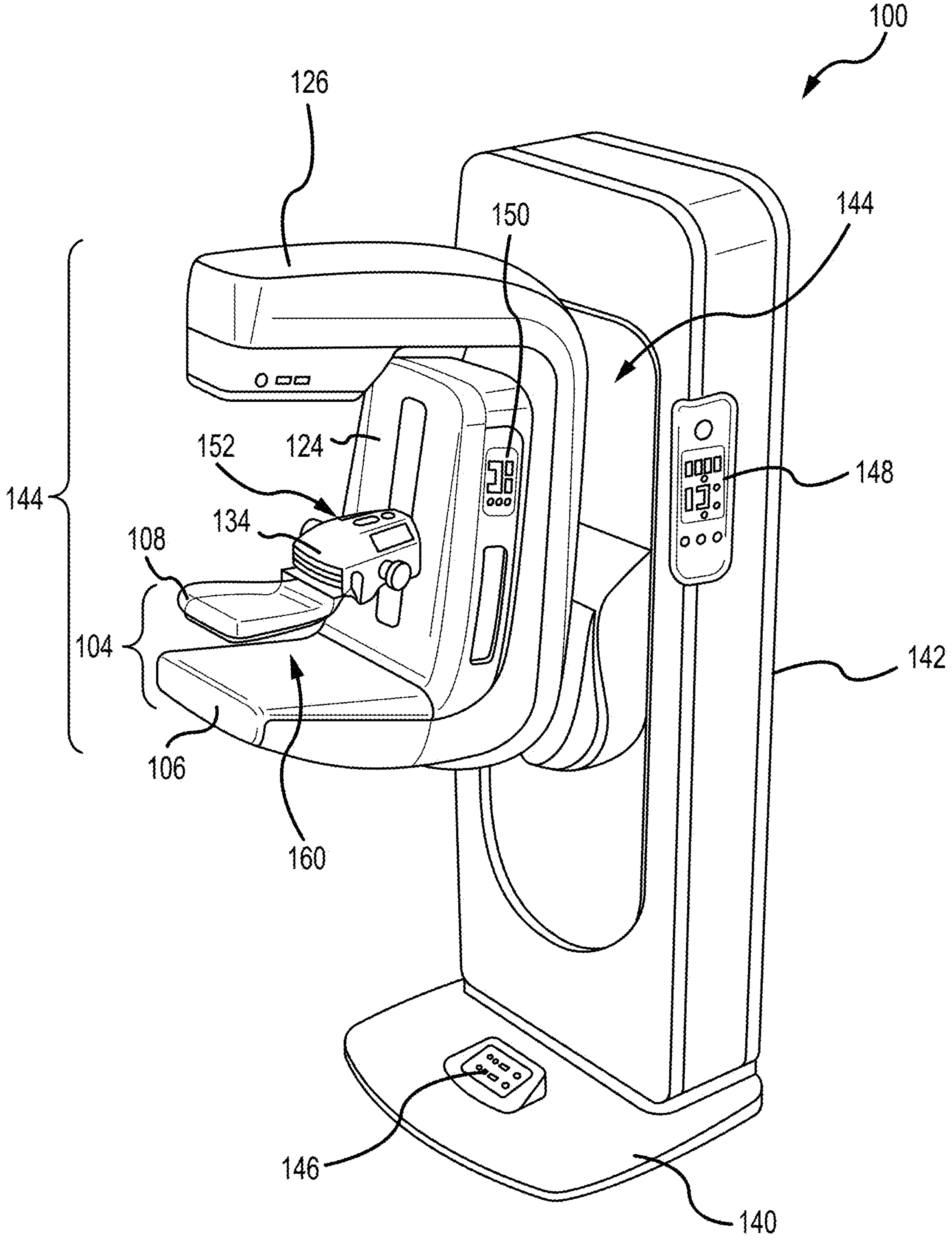
FIG. 1B is a perspective view of the imaging system of FIG. 1A.

FIG. 1A is a schematic view of an exemplary imaging system 100 and FIG. 1B is a perspective view of the imaging system 100. Referring concurrently to FIGS. 1A and 1B, not every element described below is depicted in both figures. The imaging system 100 immobilizes a patient's breast 102 for x-ray imaging (either or both of mammography, tomosynthesis, or other imaging modalities) via a breast compression immobilizer unit 104 that includes a static breast support platform 106 and a moveable paddle 108. Different paddles, each having different purposes, are known in the art. Certain examples paddles are also described herein for context. The breast support platform 106 and the paddle 108 each have a compression surface 110 and 112, respectively, that move towards each other to compress, immobilize, stabilize, or otherwise hold and secure the breast 102 during imaging procedures. In known systems, the compression surface 110, 112 is exposed so as to directly contact the breast 102. Either or both of these compression surfaces 110, 112 may be rigid plastic, a flexible plastic, a resilient foam, a mesh or screen, and so on. The platform 106 also houses an image receptor 116 and, optionally, a tilting mechanism 118, and optionally an anti-scatter grid (not depicted, but disposed above the image receptor 116). The immobilizer unit 104 is in a path of an imaging beam 120 emanating from x-ray source 122, such that the beam 120 impinges on the image receptor 116.

The immobilizer unit 104 is supported on a first support arm 124 via a compression arm 134, which is configured to be raised and lowered along the support arm 124. The x-ray source 122 is supported on a second support arm, also referred to as a tube head 126. For mammography, support arms 124 and 126 can rotate as a unit about an axis 128 between different imaging orientations such as CC and MLO, so that the system 100 can take a mammogram projection image at each orientation. In operation, the image receptor 116 remains in place relative to the platform 106 while an image is taken. The immobilizer unit 104 releases the breast 102 for movement of arms 124, 126 to a different imaging orientation. For tomosynthesis, the support arm 124 stays in place, with the breast 102 immobilized and remaining in place, while at least the second support arm 126 rotates the x-ray source 122 relative to the immobilizer unit 104 and the compressed breast 102 about the axis 128. The system 100 takes plural tomosynthesis projection images of the breast 102 at respective projection angles of the beam 120 relative to the breast 102.

Concurrently and optionally, the image receptor 116 may be tilted relative to the breast support platform 106 and in sync with the rotation of the second support arm 126. The tilting can be through the same angle as the rotation of the x-ray source 122, but may also be through a different angle selected such that the beam 120 remains substantially in the same position on the image receptor 116 for each of the plural images. The tilting can be about an axis 130, which can but need not be in the image plane of the image receptor 116. The tilting mechanism 118 that is coupled to the image receptor 116 can drive the image receptor 116 in a tilting motion. For tomosynthesis imaging and/or CT imaging, the breast support platform 106 can be horizontal or can be at an angle to the horizontal, e.g., at an orientation similar to that for conventional MLO imaging in mammography. The system 100 can be solely a mammography system, a CT system, or solely a tomosynthesis system, other modalities such as ultrasound, or a "combo" system that can perform multiple forms of imaging. An example of a system has been offered by the assignee hereof under the trade name Selenia Dimensions.

When the system is operated, the image receptor 116 produces imaging information in response to illumination by the imaging beam 120, and supplies it to an image processor 132 for processing and generating breast x-ray images.

A system control and workstation unit 138 including software controls the operation of the system and interacts with the operator to receive commands and deliver information including processed-ray images. The system control and workstation unit 138 may include an automatic exposure control (AEC) engine that may be configured to calculate the AEC x-ray dosage needed to perform x-ray imaging, such as a tomosynthesis sweep, on a patient's breast. The configuration of the AEC engine is described in greater detail in relation to FIG. 2.

The imaging system 100 includes a floor mount or base 140 for supporting the imaging system 100 on a floor. A gantry 142 extends upwards from the floor mount 140 and rotatably supports both the tube head 126 and a support arm 124. The tube head 126 and support arm 124 are configured to rotate discretely from each other and may also be raised and lowered along a face 144 of the gantry 142 so as to accommodate patients of different heights. The x-ray source 122 is disposed within the tube head 126. Together, the tube head 126 and support arm 124 may be referred to as a C-arm 144.

A number of interfaces and display screens are disposed on the imaging system 100. These include a foot display screen 146, a gantry interface 148, a support arm interface 150, and a compression arm interface 152. In general, the various interfaces 148, 150, and 152 may include one or more tactile buttons, knobs, switches, as well as one or more display screens, including capacitive touch screens with graphic user interfaces (GUIs) so as to enable user interaction with and control of the imaging system 100. In general, the foot display screen 146 is primarily a display screen, though a capacitive touch screen might be utilized if required or desired.

Figure 2:
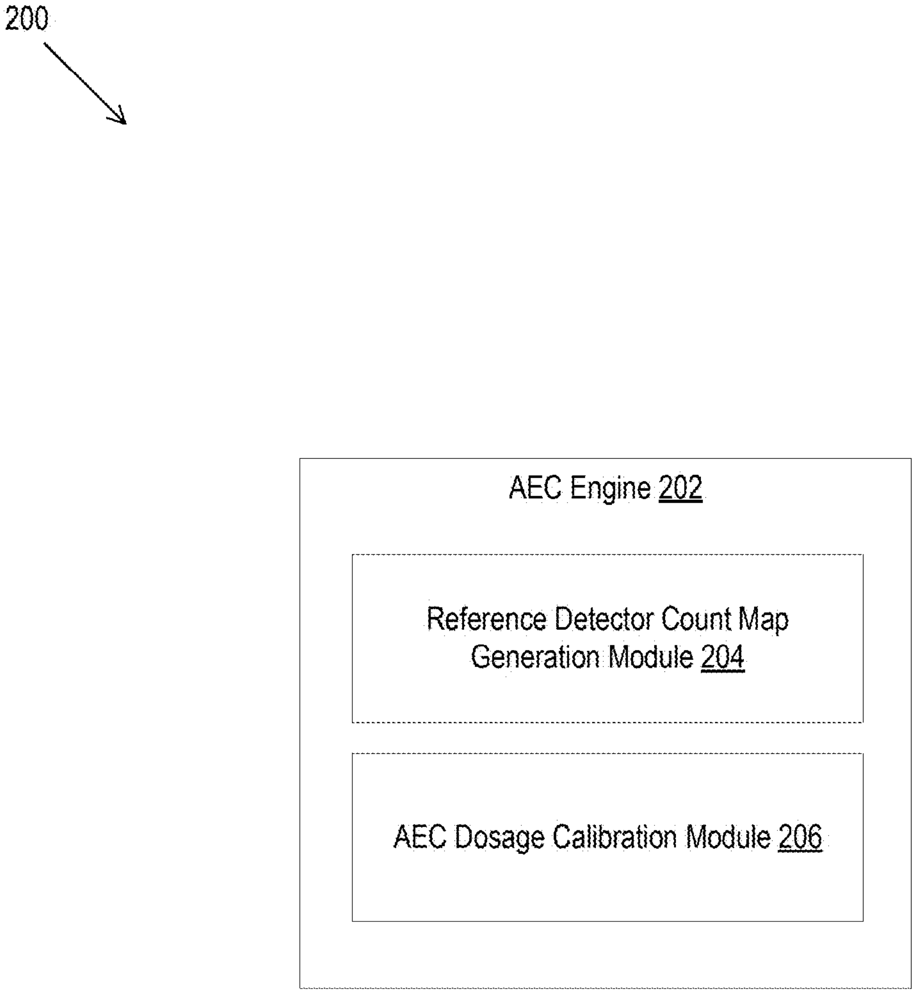
FIG. 2 illustrates an example configuration of an automatic exposure control (AEC) engine of the system of FIG. 1A.

FIG. 2 illustrates an example configuration 200 of an automatic exposure control (AEC) engine 202 of the system of FIG. 1A. The AEC engine 202 may be configured within the workstation 138 of the imaging system 100. As such, the description of FIG. 2 refers to components depicted in FIGS. 1A and 1B and are numbered accordingly.

The AEC engine 202 may include a reference detector count map generation module 204 and an AEC dosage calibration module 206. Other types of modules are also possible. The AEC engine is configured to calculate the AEC x-ray dosage that is to be used during x-ray imaging of a patient's breast, including during the full tomosynthesis sweep process. The AEC x-ray dosage may include an x-ray dosage that is calculated to balance the need to reduce the amount of radiation the patient is exposed to with the need to acquire images that are clear enough to detect potentially abnormal regions within the patient's breast.

The reference detector count map generation module 204 may be configured to generate reference detector count maps for each of a plurality of projection angles at which the imaging system 100 may be configured to operate. For example, for a wide-angle tomosynthesis sweep, the range of projection angles at which the imaging system 100 may operate may typically range from +30 to −30 degrees and, in some cases, may even range between +/−60 degrees. The reference detector count map generation module 204 may acquire reference detector count maps at each of the discrete projection angles at which the imaging system 100 may operate.

For an imaging system that can operate between +/−30 degrees, the reference detector count map generation module 204 may acquire reference images and generate reference detector count maps for each of the 61 discrete projection angles that exists between +30 degrees and −30 degrees, with 1 degree increments. In some examples, the reference detector count map generation module 204 may also acquire reference detector count maps at intervening projection angles as well. In other examples, the reference detector count maps for intervening projection angles may be pre-calculated and stored or calculated in real-time using a curve fitting operation that is described further detail in relation to FIG. 6.

The reference detector count map generation module 204 may cause the imaging system 100 to generate the reference detector count map at each of the plurality of projection angles by exposing a phantom of uniform thickness with a reference dosage of x-ray radiation, acquiring the resulting reference image, determining the detector count values for each of the pixels within the reference image and generating a map that associates the determined detector count value to each of the pixels within the reference image.

The reference dosage used to generate the reference images may be an x-ray dosage that is known to result in x-ray images with sufficient clarity and typically used in a clinical setting. For example, a typical reference x-ray radiation dosage may be between 5 mGy to 10 mGy for 4 cm thick uniform phantom Once the reference detector count map for each of a plurality of projection angles is generated, the reference detector count map is stored in a local data store or external data store that is communicatively connected to the imaging system 100. As described below in relation to the AEC dosage calibration module 206 and FIG. 7, the reference detector count map for each projection angle may then be used by the AEC dosage calibration module 206 to calculate the AEC x-ray dosage needed for the wide-angle tomosynthesis imaging process. As described above, the term "AEC x-ray dosage" is defined to be an x-ray dosage that balances the need to reduce the amount of radiation the patient is exposed to with the need to acquire images that are clear enough to detect potentially abnormal regions within the patient's breast. In other words, the "AEC x-ray dosage," as used within the instant application, is the minimum amount of x-ray dosage needed to acquire x-ray images with image quality that is enough to detect potential abnormalities within the patient's breast. The process of generating the reference detector count maps is described in greater detail in relation to FIGS. 3-6.

The AEC dosage calibration module 206 is configured to automatically calculate the AEC x-ray dosage needed to acquire adequately clear x-ray images of the patient's breast during a tomosynthesis sweep process. The AEC dosage calibration module 206 may use the stored reference detector count maps in calculating the AEC x-ray dosage.

In some examples, the AEC dosage calibration module 206 may cause the components of the imaging system 100 to move to a particular projection angle in order to start the dosage calibration process. In other examples, the AEC dosage calibration module 206 may start the dosage calibration process from whatever projection angle the components of the imaging system 100 are currently positioned at.

The AEC dosage calibration process may start by acquiring a scout image of the patient's breast using a low x-ray dosage. A low x-ray dosage may be a dosage that is a fraction of a typical x-ray dosage, such as 5% or 10% of a typical x-ray dosage. The AEC x-ray dosage to use during the tomosynthesis process may be calculated by comparing the detector count values associated with the scout image to the reference detector count values associated with the reference images from the reference detector count maps acquired and stored by the reference detector count map generation module 204. The process of calculating the AEC calibrated x-ray radiation dosage to use during the tomosynthesis process is described in greater detail in relation to FIGS. 6-7.

Figure 3:
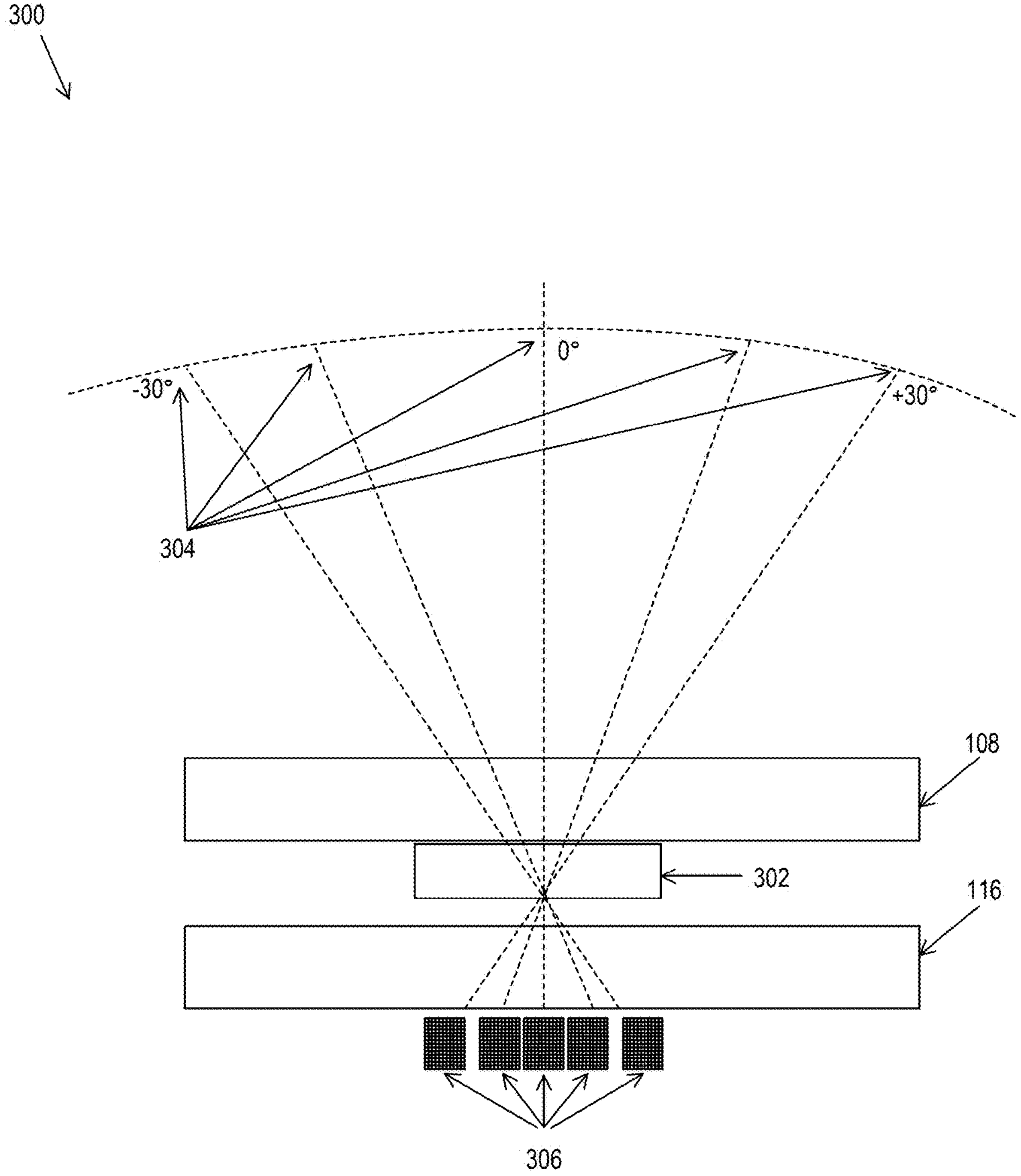
FIG. 3 illustrates an example schematic view of an imaging system during the generation of the reference images.

FIG. 3 illustrates an example schematic view 300 of the imaging system 100 during the generation of the reference images. The imaging system 100 immobilizes a phantom 302, which simulates a patient's breast, for x-ray imaging via a breast compression immobilizer unit 104 (not illustrated in FIG. 3) that includes a moveable paddle 108. A support arm rotates an x-ray source 122 (not illustrated in FIG. 3) relative to the immobilizer unit 104 including the moveable paddle 108 and the phantom 302 about an axis. The image receptor 116 produces imaging information in response to illumination by the imaging beam 120 from the x-ray source 122 as the support arm rotates the x-ray source 122 along each of a plurality of projection angles 304. Thus, the imaging system 100 may acquire a plurality of reference images 306, with at least one reference image at each of the respective projection angles 304.

Although FIG. 3 illustrates projection angles 304 from −30 degrees to +30 degrees, the projection angles may extend over a larger or smaller range depending on the type of imaging system 100. The generation of reference detector count maps from the each of plurality of reference images 306 is described in further detail in relation to FIG. 4.

Figure 4:
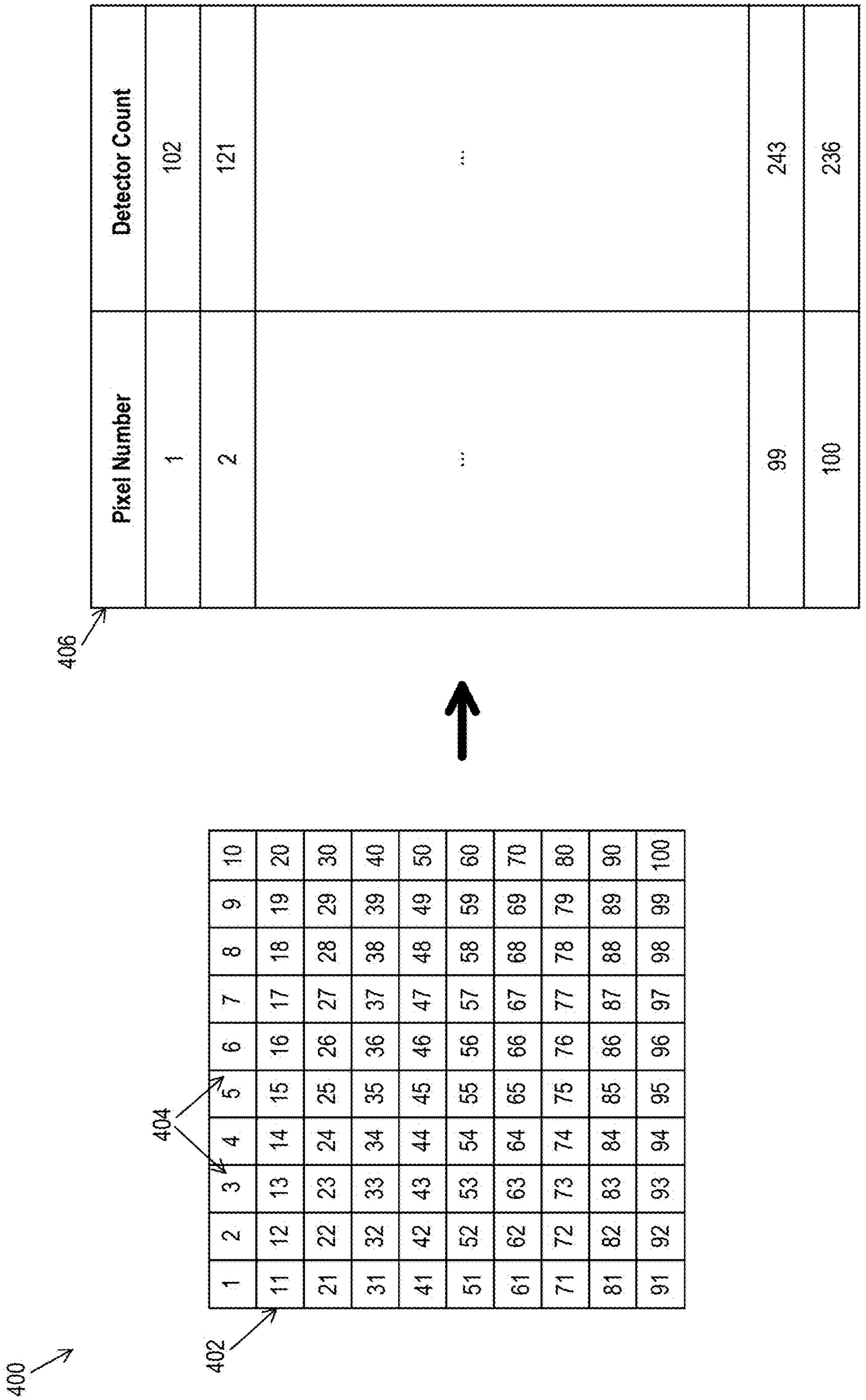
FIG. 4 illustrates an example schematic view of a reference image and a corresponding reference detector count map generated by a reference detector count map generation module of an imaging system.

FIG. 4 illustrates an example schematic view 400 of a reference image and a corresponding reference detector count map generated by the reference detector count map generation module 204 of the imaging system 100.

Each reference image 402 of the plurality of reference images 306 generated by the imaging system 100 include a plurality of pixels 404. Although, the plurality of pixels 404 within the reference image 402 in FIG. 4 are labeled with numbers ranging from 1 to 100, in reality, the plurality of pixels 404 may extend over larger or smaller range of pixels.

The reference detector count map generation module 204 of the AEC engine 202, upon acquiring the reference image 402 as described in relation to FIG. 3, may determine the reference detector count values associated with each of the plurality of pixels 404 by communicating with the image receptor 116 and image processor 132 in order to determine the digital count of the x-ray signal received by the image receptor when the phantom 302 is exposed to a x-ray radiation from the x-ray source 122.

The reference detector count map generation module 204 of the AEC engine 202 may generate a reference detector count map 406 for each reference image 402 based on the reference detector count values communicated by the image receptor 116 and image processor 132. In some examples, the reference detector count map 406 may include a table with each of the plurality of pixels 404 listed in one column and the corresponding detector count values listed in a second column. In other examples, the plurality of pixels 404 and the corresponding detector count values may be organized differently. Once generated, the reference detector count map 406 may be stored in a local data store within the imaging system 100 or in an external data store that is communicatively connected to the imaging system 100.

Figure 5:
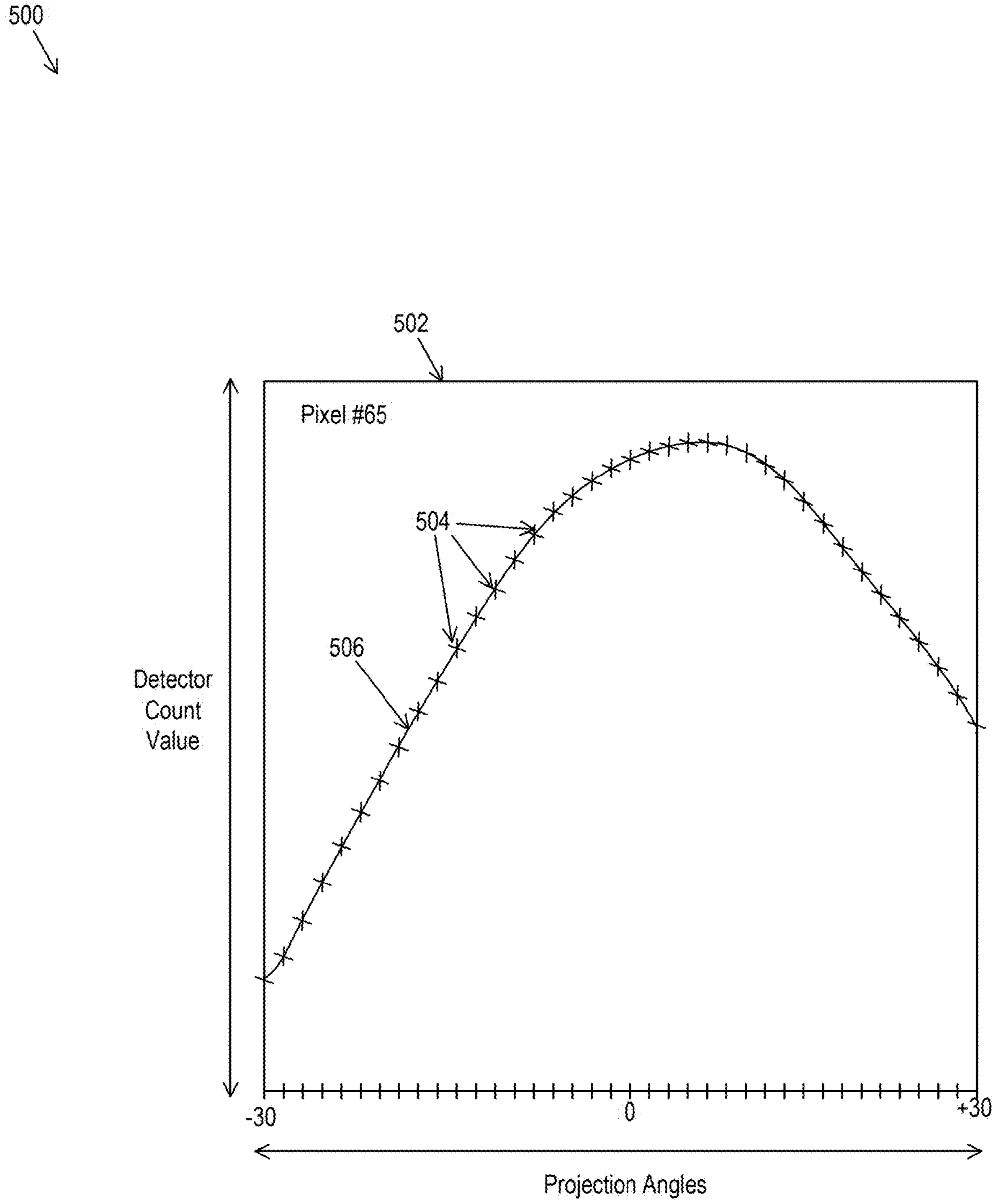
FIG. 5 illustrates an example schematic view of a curve fitting operation to estimate reference detector count values at intervening projection angles.

FIG. 5 illustrates an example schematic view 500 of a curve fitting operation to estimate reference detector count values at intervening projection angles. As described in relation to FIG. 3, the reference images 306 are only captured at certain projection angles. The reference images 306 are typically captured at projection angles that are 1 degree increments within the range of projection angles that the imaging system is operational at. A reference image 306 and a corresponding reference detector count map 406 may not be acquired or generated for intervening projection angles. To calculate the AEC dosage, the AEC dosage calibration module 206 of the AEC engine 202 may require the reference detector count map 406 at an intervening projection angle for which a reference detector image 306 may not have been acquired by the reference detector count map generation module 204. In such cases, the reference detector count values for intervening projection angles may be estimated based on the stored reference detector count map 406 for adjacent discrete projection angles by performing a curve fitting operation on the data from the stored reference detector count maps.

The example schematic view 500 illustrates the curve fitting operation associated with one of the pixels, pixel number 65 from FIG. 4, out of the plurality of pixels 404. The example schematic view 500 includes a plot 502, with an x-axis and a y-axis. The x-axis may include the range of projection angles. In the present example, the projection angles may range from −30 to +30 degrees. The y-axis may include a range of detector count values.

To perform the curve fitting operation, for each pixel of the plurality of pixels 404, the reference detector count values corresponding to each of the plurality of projection angles on the x-axis may be plotted as graphical representation. For each pixel of the plurality of pixels 404. For example, the plot 502 associated with pixel number 65, as illustrated in FIG. 5, may include a plot of each of the detector count values 504 corresponding to the each of the plurality of projection angles, wherein each of the detector count values 504 may be extracted from the reference detector count map 406 corresponding to the particular projection angle.

For example, at projection angle −30 degrees, the reference detector count map 406 for the −30 degrees may be retrieved from the data store and the reference detector count value associated with pixel number 65 may be identified. The process may be repeated using each reference detector count map 406 for each projection angle for projection angles ranging from −30 degrees to +30 degrees in order to populate the plot 502 with the detector count values 504.

Once the plot 502 is generated, a curve fitting function may be used to generate a curve 506 that fits the detector count values 504. Curve fitting may be the process of constructing a curve or mathematical function that has the best fit to a series of data points. In some examples, the curve fitting may be done using an interpolation function or an extrapolation function. In other examples, polynomial curve fitting where a polynomial function is fitted to the series of data points may be used in generating the curve 506.

In cases where polynomial curve fitting is used, the order of the polynomial function may range from low-orders such as a first order to high-orders, such as fifth or sixth orders. Generally, in the case of generating curve 506 that fits the detector count values 504, a fourth order polynomial function, such as "$y=ax^4+bx^3+cx^2+dx+e$" may be used. Once a polynomial function representing a curve 506 that fits the detector count values 504 is generated using regression analysis, the coefficients of the generated polynomial function may be stored in the data store. The polynomial coefficients may later be used by the AEC dosage calibration module 206 to estimate the detector count values at intervening projection angles or angles outside the +/−30 degree scan angle range in near real-time.

Figure 6:
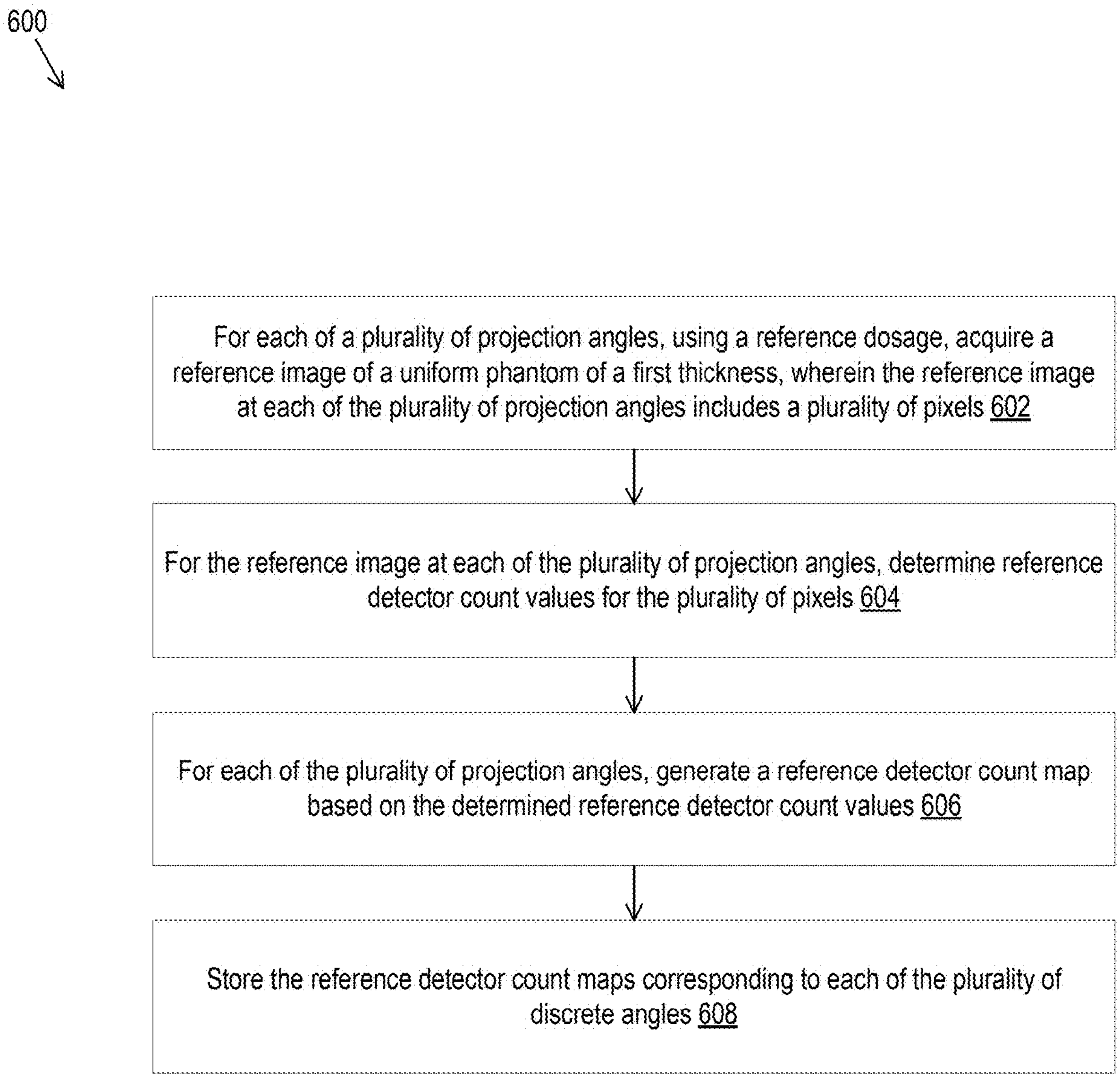
FIG. 6 illustrates an example method for generating a reference detector count map at each of a plurality of projection angles using a reference detector count map generation module of an imaging system.

FIG. 6 illustrates an example method 600 for generating a reference detector count map 406 at each of a plurality of projection angles 304 using the reference detector count map generation module 204 of the imaging system 100. The method 600 begins with operation 602. In operation 602, the reference detector count map generation module 204 of the imaging system 100 may acquire a reference image 306 of a phantom 302 at each of a plurality of projection angles 304. For example, the reference detector count map generation module 204 may cause the imaging system 100 to expose the phantom 302 with a reference x-ray dosage and acquire the resulting x-ray images for each of the plurality of projection angles 306.

The reference x-ray dosage may include any dosage of radiation that is effective in producing x-ray images that meet at least a threshold image quality level. The phantom 302 used in the generation of reference images may generally be made from a uniform material and be of a uniform thickness. In some examples, the reference detector count map 406 for each of the plurality of projection angles 304 may be generated using a phantom 302 with a thickness that mimics the average patient breast. In other examples, the reference detector count map 406 may be generated using a phantom that is of a different thickness.

Although the reference detector count map 406 for each of the plurality of projection angles 304 are generated using a phantom 302 of a particular thickness, the reference detector count maps corresponding to other breast thicknesses may be derived from the reference detector count maps acquired using the phantom 302 of average thickness by applying a scale factor from a previously generated look up table. The process of acquiring the reference detector count maps for different breast thicknesses is further described in FIG. 7.

In some examples, the plurality of projection angles 404 at which the reference images 306 are acquired for the generation of the reference detector count maps may include each of the discrete projection angles within the range of projection angles included within tomosynthesis sweep conducted by the imaging system 100. In some examples, the range of projection angles may be from +30 degrees to −30 degrees. In such a case, the discrete projection angles may include each of the 61 discrete projection angles between +30 degrees and −30 degrees. In other examples, the range of projection angles may be from +60 degrees to −60 degrees, in which case, the discrete projection angles may include each of the 121 discrete projection angles between +60 degrees and −60 degrees. In other examples, instead of acquiring reference images at 1-degree increments, reference images may be acquired at other regular intervals, such as every 2-degrees or every 5-degrees.

In some examples, the plurality of projection angles at which the reference images are acquired for the generation of the reference detector count maps may include more or less number or projection angles and may include intervening angles that lay between the discrete angles, such as projection angles at 0.5 degree increments; or may include angles outside the angular range where reference images are acquired. In other examples, a curve fitting operation as described in relation to FIG. 5 may be performed and in case of a polynomial curve fitting operation, the corresponding polynomial coefficients may be stored and used for generating the estimated detector count values at intervening projection angles, or out-of-range scan angles in real-time or near real-time.

In operation 604, the reference detector count map generation module 204 of the imaging system 100 may, for each of the reference images 306 acquired in operation 602, determine reference detector count values associated with each of the plurality of pixels within each of the reference images 306.

Each of the reference images acquired in operation 602 include a plurality of pixels 404. For example, the reference detector count map generation module 204 may communicate with the image receptor 116 and the image processor 132 in order to determine the digital count of the x-ray signal received by the image receptor 116 when the phantom 302 is exposed to a reference x-ray dosage in operation 602. The count of the x-ray signal associated with a particular pixel of the reference image 402 is determined to be the reference detector count value associated with the particular pixel of the reference image 402. Thus, the reference detector count values of each of the plurality of pixels 404 within each of the reference images 306 acquired in operation 602 may be determined in operation 604.

In operation 606, the reference detector count map generation module 204 may generate a reference detector count map for each of the plurality of projection angles 304 based on the reference detector count values determined in operation 604 for each of the reference images 306 acquired in operation 602. The reference detector count map 406 may include a map between each of the pixels within a reference image and the corresponding reference detector count value measured at the image receptor 116 when a reference x-ray dosage is emitted onto the phantom.

In operation 608, the reference detector count map generation module 204 may store the reference detector count map 406 that is generated for each of the plurality of projection angles 304, the corresponding projection angle information and reference x-ray dosage information in a data store that is local to the imaging system 100 or a data store that is external to the imaging system 100 while being communicatively connected to the imaging system 100. The stored reference detector count maps, and the reference x-ray dosage information may be retrieved and used in the calculation of the AEC x-ray dosage as described in FIG. 7.

When reference detector count values for intervening projection angles for which reference images and corresponding reference detector count maps were not acquired, are needed in calculating the AEC x-ray dosage, curve fitting operation may be performed to acquire the reference detector count values as further described in relation to FIG. 5 above.

Figure 7:
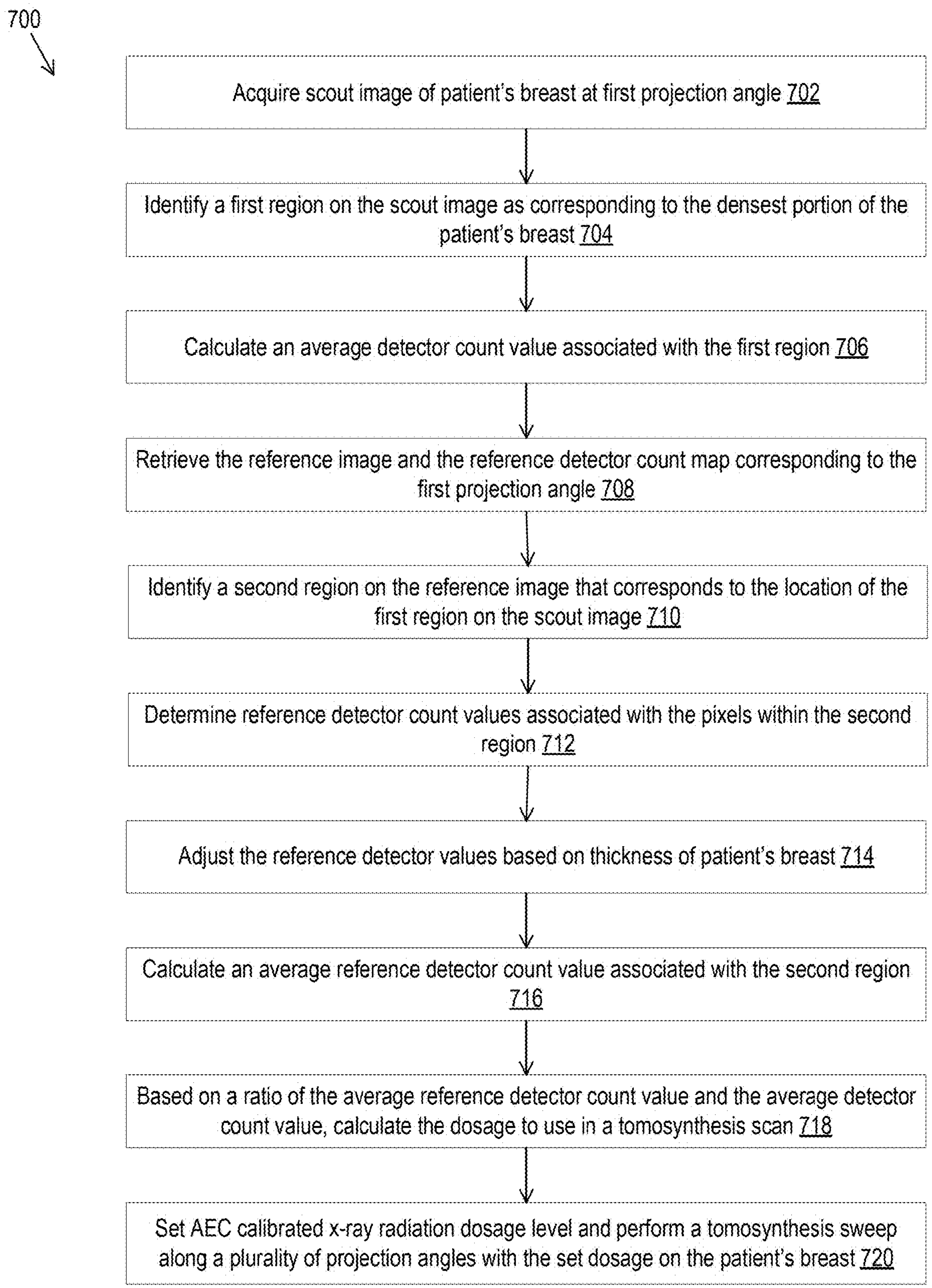
FIG. 7 illustrates an example method for calculating the AEC x-ray dosage needed to perform x-ray imaging, including a wide-angle tomosynthesis sweep of a patient's breast, using an imaging system.

FIG. 7 illustrates an example method 700 for calculating the AEC x-ray dosage needed to perform x-ray imaging, including a wide-angle tomosynthesis sweep of a patient's breast, using the imaging system 100. In operation 702, the AEC dosage calibration module 206 may cause the imaging system 100 to acquire a scout image of the patient's breast at a first projection angle. In some examples, and in a typical tomosynthesis system, the first projection angle may be a particular projection from among the plurality of projection angles 304, such as 0-degrees. However, rather than moving the support arms 124 and 126 of the imaging system 100 to a particular projection angle, the AEC dosage calibration module 206 may cause the imaging system 100 to acquire the scout image from the current position of the support arms 124 and 126. The current position of the support arms 124 and 126 may simply be based on whatever position the support arms 124 and 126 were left in following a previous operation of the imaging system 100. Moving the support arms 124, 126 and resetting the support arms 124, 126 to a 0 degree angle or a particular angle before beginning the tomosynthesis process each time requires time and effort. In addition, the moving the support arms 124, 126 to an exact position is difficult to accomplish and often results in a margin of error of a few degrees. Thus, having the ability to acquire the scout image from any current position results in acquiring more accurate scout images.

The scout image of the patient's breast may be acquired using a low x-ray dosage. Typically, 5% or 10% of the reference x-ray dosage may be used in acquiring the scout image. The scout image is used as a starting point in the calculation of the actual dosage needed to perform the full tomosynthesis sweep according to the AEC process. Therefore, a low x-ray dosage is used to acquire the scout image in order to limit the radiation exposure to the patient.

In operation 704, the AEC dosage calibration module 206 may identify a first region on the scout image, acquired during operation 702, as corresponding to the densest portion of the patient's breast. In general, the densest portion of a patient's breast is identified in order to determine the minimum amount of x-ray dosage required to get acceptable detector count values even at the densest portions of the patient's breast. In other words, the densest portion of a patient's breast is typically the hardest regions for x-rays to pass through and thus require the most amount of dosage in order to generate adequate quality images. Thus, if the x-ray radiation dosage is calibrated for the densest regions of the patient's breast, the x-ray radiation dosage is typically adequate for the rest of the regions of the patient's breast.

The densest region of the patient's breast may be determined by first flattening the scout image by applying a gain map associated with the first projection angle in order to calibrate the scout image for angle effects and heel effects.

When digital flat panel x-ray imaging receptors are used, one of the practical requirements is to provide gain calibration. The imaging receptor may comprise a two-dimensional array of millions of imaging pixels, and there may be inherent differences in the response of different imaging pixels to impinging x-rays. When all imaging pixels receive the same x-ray exposure, ideally each should provide the same electrical output signal (pixel value). However, in practice this may not be the case and typically there are differences between the pixel values that different imaging pixels provide when exposed to the same x-ray input. In addition, incident x-ray intensity across the detector surface usually is non-uniform: for example, due to the "heel effect" the x-ray intensity drops along the direction from the chest wall to the nipple. To correct for differences in pixel values in response to uniform x-ray exposure, and to correct for the non-uniform x-ray intensity distribution across the x-ray imaging detector surface area, various gain calibration and image correction techniques are employed. Typically, in conventional x-ray mammography the flat panel imager is exposed to an x-ray field through a "flat-field" phantom that simulates a patient's breast but has a uniform thickness and is made of a uniform material, the differences between pixel values are recorded, and a gain correction map is generated that accounts for such differences at each of the projection angles. Each gain correction map corresponding to each of the projection angles may be is stored locally in a data store within the imaging system 100 or at an external data store that is communicatively connected to the imaging system 100.

Once the scout image is generated upon exposing the patient's breast to x-ray radiation at a first projection angle, the gain correction map corresponding to the first projection angle is retrieved from the data store and the gain correction map and applied to the scout image in order to flatten the scout image and minimize the angle and heel effects. The angle corrected scout image may then be used to identify the densest portion of the patient's breast.

For example, the densest portion of a patient's breast is typically found in the center of the breast and is associated with the lowest detector count values. Thus, a simplified method of identifying the densest portion of the patient's breast includes identifying a first region with a group of pixels that have the lowest corresponding detector count values within a particular area of the scout image that is likely to include the center of the breast. Once the first region including the group of pixels with the lowest detector count values is identified, the particular location on the scout image that includes the first region is determined to be the densest portion of the patient's breast.

In operation 706, the AEC dosage calibration module 206 may calculate an average detector count value associated with the group of pixels within the first region of the scout image. For example, the average detector count value may be calculated by determining the detector count values associated with each pixel within the group of pixels located withing the first region identified in operation 704 and averaging the detector count values to arrive at the average detector count value.

In operation 708, the AEC dosage calibration module 206 of the AEC engine 202 may retrieve the reference image and the reference detector count map corresponding to the first projection angle from the data store at which reference detector count maps generated by the reference detector count map generation module 204 are stored in operation 608 from FIG. 6. When a reference image and the reference detector count map for the first projection angle are not available in the data store because the first projection angle is an intervening angle or out-of-the-scan-range for which the reference detector count map generation module 204 has not generated a reference image or reference detector count map, the AEC dosage calibration module 206 may proceed to operation 712 where a polynomial curve fitting operation or an interpolation or an extrapolation operation may be used in generating the reference detector count values needed in real-time or in near real-time.

In operation 710, the AEC dosage calibration module 206 of the AEC engine 202 may identify a second region on the retrieved reference image that corresponds in location to the first region from the scout image, as identified in operation 704. As an example, if in operation 704, the identified first region includes pixels corresponding to pixel numbers 56, 57, 66, 67 on the scout image, the second region associated with the reference image may also include pixels corresponding to pixel numbers 56, 57, 66, 67.

In operation 712, the AEC dosage calibration module 206, after identifying the second region corresponding to the reference image, may determine the reference detector count values corresponding to the pixels within the second region.

In case the first projection angle is an intervening angle for which a reference image and corresponding reference detector count map was not acquired or generated, the AEC dosage calibration module 206 may estimate the reference detector count values for the pixels within the second region using a polynomial curve fitting function or interpolation function in real-time or near real-time as described in FIG. 5. In other examples, instead of using curve fitting to only generate reference detector count values for pixels within the second region, curve fitting functions may be applied to generate a complete reference image and corresponding reference detector count map.

In operation 714, the AEC dosage calibration module 206 may also make adjustments to the detector count values based on the patient's breast size. As described above, the reference images and corresponding reference detector count maps are based off of a phantom 302 that corresponds to an average patient breast thickness. In some examples, the phantom 302 may have a thickness of 4 cms and the reference detector count values included in the reference detector count maps may act as reference values for a patient with a breast thickness of about 4 cm. However, when the patient's breast thickness is significantly higher or lower, the reference detector count values may need to be adjusted.

Generally, a look-up table that includes a scale factor corresponding to how to adjust detector count values when the patient's breast thickness is different than the thickness of the phantom 302 may be used to make adjustments to the reference detector count values associated with the pixels of the second region. For example, the look-up table may indicate that the scale factor associated with a patient breast thickness of 6 cm may be 1.2. In such a case, the reference detector count values for the pixels within the second region determined by the AEC dosage calibration module 206, as determined in operation 712, may be multiplied by a factor of 1.2 to arrive at the adjusted reference detector count values.

Alternatively, the reference images and corresponding reference detector count maps may be acquired, generated and stored for phantoms of different sizes. In other words, instead of only acquiring reference images and generating reference detector count maps based on phantom 302 that corresponds to average patient breast thickness, the process described in FIG. 6 may be repeated for different phantom thicknesses and reference images and reference detector count maps corresponding to each phantom thickness may be stored. In such a case, in operation 708, the reference image and reference detector count map corresponding to a phantom thickness that matches the patient's breast thickness may be retrieved and the adjustment operation outlined above in relation to operation 714 may be skipped since the reference detector count values already account for factors corresponding to the patient's breast thickness.

In operation 716, the AEC dosage calibration module 206 may calculate the average reference detector count value associated with the pixels of the second region. The calculation of the average reference detector count value may be based on the adjusted reference count values as determined in operation 714. To calculate the average reference detector count value, the AEC dosage calibration module 206 may simply calculate the mean value corresponding to the adjusted reference detector count values corresponding to the pixels within the second region of the reference image.

In operation 718, the AEC dosage calibration module 206 may calculate the dosage to use in a full tomosynthesis scan based on a ratio of the average reference detector count value and the average detector count value. For example, the AEC calibrated x-ray radiation dosage for the full tomosynthesis sweep may be calculated based on a formula as follows:

$$AEC \text{ calibrated } xray \text{ radiation dosage} = K \times \text{scout dosage} \times \frac{\text{average reference detector count value}}{\text{average detector count value}}$$

wherein, the average reference detector count value is the average reference detector count value calculated in operation 716 based on the adjusted detector count values from operation 714, the average detector count value is the average detector count value calculated in operation 706 and the scout dosage is the radiation dosage used to acquire the scout image in operation 702. K is a global scaling factor, which can be adjusted based on different clinical needs.

In operation 720, the AEC dosage calibration module 206 may set the AEC calibrated x-ray radiation dosage level of the imaging system 100 to the value calculated in operation 718 and cause the imaging system 100 to perform a tomosynthesis sweep across the full range of projection angles using the set AEC calibrated x-ray radiation dosage. The AEC calibrated x-ray radiation dosage calculated in operation 718 balances the need to minimize the amount of radiation exposure for the patient while also generating adequately exposed tomosynthesis x-ray images at the plurality of projection angles.

Figure 8:
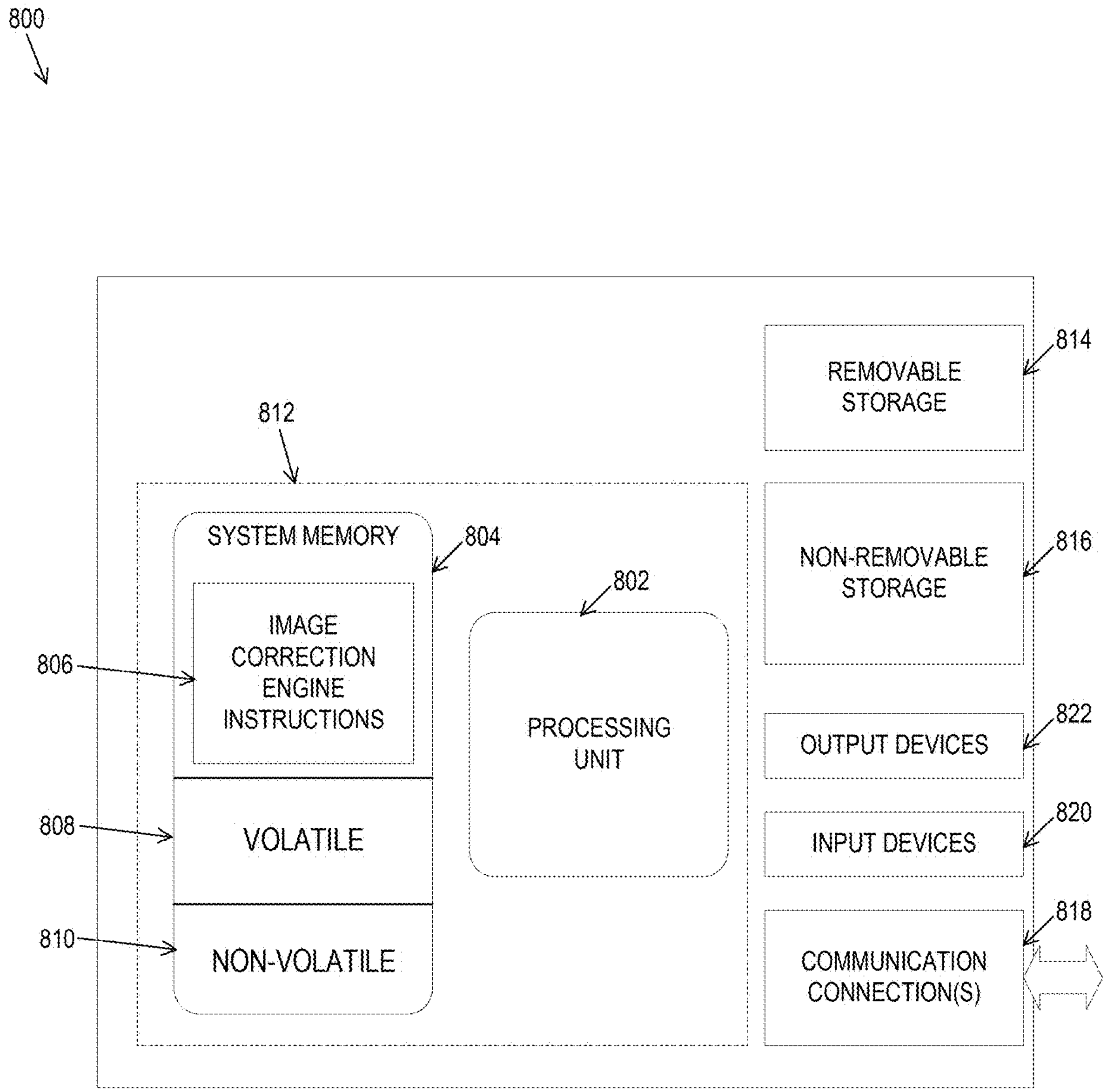
FIG. 8 illustrates one example of a suitable operating environment in which one or more of the present examples can be implemented.

FIG. 8 illustrates one example of a suitable operating environment 800 in which one or more of the present examples can be implemented. This operating environment may be incorporated directly into the visualization systems disclosed herein, or may be incorporated into a computer system discrete from, but used to control the breast imaging systems described herein, such as computer system may be, e.g., the workstation depicted in FIG. 1A. This is only one example of a suitable operating environment and is not intended to suggest any limitation as to the scope of use or functionality. Other well-known computing systems, environments, and/or configurations that can be suitable for use include, but are not limited to, imaging systems, personal computers, server computers, hand-held or laptop devices, multiprocessor systems, microprocessor-based systems, programmable consumer electronics such as smart phones, network PCs, minicomputers, mainframe computers, tablets, distributed computing environments that include any of the above systems or devices, and the like.

In its most basic configuration, operating environment 800 typically includes at least one processing unit 802 and memory 804. Depending on the exact configuration and type of computing device, memory 804, storing, among other things, instructions 806 (to read from data storage devices or sensors, or perform other methods disclosed herein) can be volatile 808 (such as RAM), non-volatile 810 (such as ROM, flash memory, etc.), or some combination of the two. The instructions 806 may include AEC engine instructions that when executed by the processing unit 802 cause the processing unit 802 to cause the AEC engine 202 to perform the operations described in further in relation to FIGS. 2-7. The most basic configuration is illustrated in FIG. 8 by dashed line 812. Further, environment 800 can also include storage devices (removable, 814, and/or non-removable, 816) including, but not limited to, magnetic or optical disks or tape. Similarly, environment 800 can also have input device(s) 820 such as touch screens, keyboard, mouse, pen, voice input, etc., and/or output device(s) 822 such as a display, speakers, printer, etc. Also included in the environment can be one or more communication connections 818, such as LAN, WAN, point to point, Bluetooth, RF, etc.

Operating environment 800 typically includes at least some form of computer readable media. Computer readable media can be any available media that can be accessed by processing unit 802 or other devices having the operating environment. By way of example, and not limitation, computer readable media can include computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, solid state storage, or any other tangible medium which can be used to store the desired information. Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic. RF, infrared and other wireless media. Combinations of the any of the above should also be included within the scope of computer readable media. A computer-readable device is a hardware device incorporating computer storage media.

The operating environment 800 can be a single computer operating in a networked environment using logical connections to one or more remote computers. The remote computer can be a personal computer, a server, a router, a network PC, a peer device or other common network node, and typically includes many or all of the elements described above as well as others not so mentioned. The logical connections can include any method supported by available communications media. Such networking environments are commonplace in offices, enterprise-wide computer networks, intranets and the Internet.

In some examples, the components described herein include such modules or instructions executable by computer system 800 that can be stored on computer storage medium and other tangible mediums and transmitted in communication media. Computer storage media includes volatile and non-volatile, removable and non-removable media implemented in any method or technology for storage of information such as computer readable instructions, data structures, program modules, or other data. Combinations of any of the above should also be included within the scope of readable media. In some examples, computer system 800 is part of a network that stores data in remote storage media for use by the computer system 800.

Figure 9:
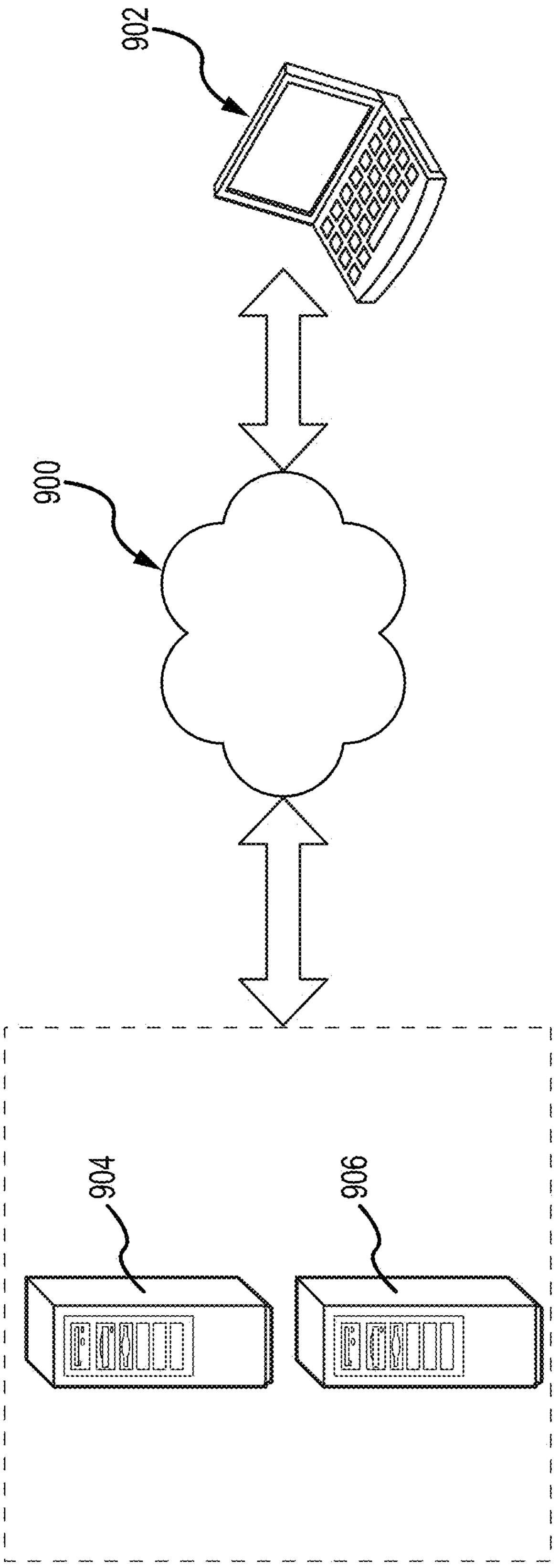
FIG. 9 is an example of a network in which the various systems and methods disclosed herein may operate.

FIG. 9 is an example of a network 900 in which the various systems and methods disclosed herein may operate. In examples, a client device, such as client device 902, may communicate with one or more servers, such as servers 904 and 906, via a network 900. In examples, a client device may be a standalone imaging system (e.g., imaging system 100 depicted in FIG. 1A) that includes all the functionality described herein. The client device may also include or incorporate a laptop, a personal computer, a smart phone, a PDA, a netbook, or any other type of computing device, such as the computing device in FIG. 8. In examples, such a client device may be connected to an imaging system. In examples, servers 904 and 906 may also be any type of computing device, such as the computing device illustrated in FIG. 8. Network 900 may be any type of network capable of facilitating communications between the client device and one or more servers 904 and 906. For example, the surface image data and the internal image data may be acquired locally via the imaging systems and communicated to another computing device(s) for further processing, such as an image acquisition workstation or a cloud-based service. Examples of such networks include, but are not limited to, LANs, WANs, cellular networks, and/or the Internet.

In examples, the various systems and methods disclosed herein may be performed by one or more server devices. For example, in one example, a single server, such as server 904 may be employed to perform the systems and methods disclosed herein, such as the methods for imaging discussed herein. Client device 902 may interact with server 904 via network 900. In further examples, the client device 902 may also perform functionality disclosed herein, such as scanning and image processing, which can then be provided to servers 904 and/or 906.

This disclosure described some examples of the present technology with reference to the accompanying drawings, in which only some of the possible examples were shown. Other aspects can, however, be embodied in many different forms and should not be construed as limited to the examples set forth herein. Rather, these examples were provided so that this disclosure was thorough and complete and fully conveyed the scope of the possible examples to those skilled in the art.

Although specific examples were described herein, the scope of the technology is not limited to those specific examples. One skilled in the art will recognize other examples or improvements that are within the scope of the present technology. Therefore, the specific structure, acts, or media are disclosed only as illustrative examples. Examples according to the technology may also combine elements or components of those that are disclosed in general but not expressly exemplified in combination, unless otherwise stated herein. The scope of the technology is defined by the following claims and any equivalents therein.

Illustrative examples of the systems and methods described herein are provided below. An embodiment of the system or method described herein may include any one or more, and any combination of, the clauses described below:

Clause 1. A tomosynthesis system for performing an automatic exposure control (AEC) operation, the system comprising: a processor: memory including instructions that when executed by the processor cause the processor to: acquire a scout image of a patient's breast at a first projection angle relative to a 0 degree normal direction to the patient's breast by emitting a scout x-ray dosage towards the patient's breast with the tomosynthesis system, the scout image including a plurality of pixels, wherein each of the plurality of pixels is associated with a detector count value from among a plurality of detector count values; identify a first region on the scout image as corresponding to a densest portion of the patient's breast; calculate an average detector count value by averaging the one or more detector count values corresponding to the one or more pixels within the first region; identify a second region on a first reference image associated with the first projection angle, wherein the second region corresponds to a location on the first reference image that matches a location of the first region on the scout image: obtain one or more reference detector count values associated with one or more reference pixels within the second region of the first reference image: calculate an average reference detector count value by averaging the one or more reference detector count values; based on a ratio between the average reference detector count value and the average detector count value, calculate an AEC calibrated dosage to use in a tomosynthesis scan; and set a radiation dosage for a tomosynthesis sweep at a plurality of projection angles on the patient's breast to the AEC calibrated dosage.

Clause 2. The tomosynthesis system of clause 1, wherein obtaining the one or more reference detector count values includes: extracting the one or more reference detector count values from a reference detector count map associated with the first projection angle, wherein the reference detector count map associated with the first projection angle is one of a plurality of reference detector count maps that are generated in a calibration process prior to acquiring the scout image.

Clause 3. The tomosynthesis system of clause 2, wherein the calibration includes: acquiring a plurality of reference images of a phantom, wherein each of the plurality of reference images is acquired using the tomosynthesis system at each of the plurality of projection angles and each of the plurality of reference images include a plurality of reference image pixels: determining detector count values corresponding to each of the plurality of reference image pixels within each of the plurality of reference images; and generating the plurality of reference detector count maps corresponding to each of the plurality of projection angles by compiling the plurality of reference image pixels and corresponding detector count values associated with each of the plurality of projection angles.

Clause 4. The tomosynthesis system of clauses 2-3, wherein when the first projection angle is not one of the plurality of projection angles that includes the reference detector count map, obtaining the reference detector count values associated with the one or more reference pixels from the second region of the first reference image includes: estimating the reference detector count values by performing (i) an interpolation function, (ii) an extrapolation function (iii) or a polynomial curve fitting function.

Clause 5. The tomosynthesis system of clause 1, wherein the plurality of projection angles includes a range of angles that is between about −60 degrees and about +60 degrees relative to the patient's breast.

Clause 6. The tomosynthesis system of clause 1, wherein calculating the AEC calculated dosage includes multiplying the scout x-ray dosage with the ratio between the average reference detector count value and the average detector count value, and a global scaling factor.

Clause 7. The tomosynthesis system of clause 1, wherein the scout x-ray dosage includes a combination of: voltage used to generate a radiation from an x-ray source (kV), x-ray cathode to anode tube current (mA) and a length of time(s) to expose the patient to the radiation.

Clause 8. The tomosynthesis system of clause 1, wherein the scout x-ray dosage is less than 10% of the AEC calculated dosage.

Clause 9. The tomosynthesis system of clause 1, wherein identifying the densest portion of the patient's breast includes: applying a gain map associated with the first projection angle to the scout image to compensate for angle effects; and identifying pixels within pre-identified center region that includes the lowest detector count values.

Clause 10. A method of performing an automatic exposure control (AEC) operation using a tomosynthesis system, the method comprising: acquiring a scout image of a patient's breast at a first projection angle by emitting a scout x-ray dosage towards the patient's breast with the tomosynthesis system, the scout image including a plurality of pixels, wherein each of the plurality of pixels is associated with a detector count value from among a plurality of detector count values; identifying a first region on the scout image as corresponding to a densest portion of the patient's breast; calculating an average detector count value by averaging the one or more detector count values corresponding to the one or more pixels within the first region; identifying a second region on a first reference image associated with the first projection angle, wherein the second region corresponds to a location on the first reference image that matches a location of the first region on the scout image: obtaining one or more reference detector count values associated with one or more reference pixels within the second region of the first reference image; calculating an average reference detector count value by averaging the one or more reference detector count values; based on a ratio between the average reference detector count value and the average detector count value, calculating an AEC calibrated dosage to use in a tomosynthesis scan; and setting a radiation dosage for a tomosynthesis sweep at a plurality of projection angles on the patient's breast to the AEC calibrated dosage.

Clause 11. The method of clause 10, wherein obtaining the one or more reference detector count values includes: extracting the one or more reference detector count values from a reference detector count map associated with the first projection angle, wherein the reference detector count map associated with the first projection angle is one of a plurality of reference detector count maps that are generated in a calibration process prior to acquiring the scout image.

Clause 12. The method of clause 11, wherein the calibration process includes: acquiring a plurality of reference images of a phantom, wherein each of the plurality of reference images is acquired using the tomosynthesis system at each of the plurality of projection angles and each of the plurality of reference images include a plurality of reference image pixels: determining reference image detector count values corresponding to each of the plurality of reference image pixels within each of the plurality of reference images; and generating the plurality of reference image detector count maps corresponding to each of the plurality of projection angles by compiling the plurality of reference image pixels and corresponding reference image detector count values associated with each of the plurality of projection angles.

Clause 13. The method of clauses 11-12, wherein when the first projection angle is not one of the plurality of projection angles that includes the reference detector count map, obtaining the reference detector count values associated with the one or more reference pixels from the second region of the first reference image includes: estimating the reference detector count values by performing (i) an interpolation function, (ii) an extrapolation function or (iii) a polynomial curve fitting function.

Clause 14. The method of clause 10, wherein the plurality of projection angles includes a range of angles that is between about −60 degrees and about +60 degrees corresponding to the patient's breast.

Clause 15. The method of clause 10, wherein calculating the AEC calculated dosage includes multiplying the scout x-ray dosage with the ratio between the average reference detector count value and the average detector count value, and a global scaling factor.

Clause 16. The method of clause 10, wherein the first projection angle is based on a current position of the tomosynthesis system prior to acquiring the scout image.

Clause 17. The method of clause 16, wherein the current position is different than 0 degree angle relative to the patient's breast.

Clause 18. The method of clause 10, further comprising: acquiring the scout image of the patient's breast at a second projection angle that is different than the first projection angle.

Clause 19. The method of clause 10, wherein identifying the densest portion of the patient's breast includes: applying a gain map associated with the first projection angle to the scout image to compensate for angle effects; and identifying pixels within pre-identified center region that includes the lowest detector count values.

Clause 20. A method of performing a calibration operation associated with an automatic exposure control (AEC) operation using a tomosynthesis system, the method comprising: acquiring a plurality of reference images of a phantom at a plurality of projection angles, wherein each of the plurality of reference images include a plurality of reference image pixels: generating a plurality of reference image detector count maps corresponding to each of the plurality of reference images by compiling a plurality of reference image pixels and corresponding reference image detector count values associated for each of the plurality of reference images: storing the plurality of reference image detector count maps; acquiring a scout image of a patient's breast at the first projection angle by emitting a scout x-ray dosage towards the patient's breast with the tomosynthesis system, the scout image including a plurality of pixels, wherein each of the plurality of pixels is associated with a detector count value from among a plurality of detector count values; identifying a first region on the scout image as corresponding to a densest portion of the patient's breast; calculating an average detector count value by averaging the one or more detector count values corresponding to the one or more pixels within the first region; identifying a second region on a first reference image associated with a first projection angle, wherein the second region corresponds to a location on the first reference image that matches a location of the first region on the scout image and the first projection angle is one of the plurality of projection angles and the first reference image is one of the plurality of reference images; obtaining one or more reference detector count values associated with one or more reference pixels within the second region of the first reference image; calculating an average reference detector count value by averaging the one or more reference detector count values; based on a ratio between the average reference detector count value and the average detector count value, calculating an AEC calibrated dosage to use in a tomosynthesis scan; and setting a radiation dosage for a tomosynthesis sweep at a plurality of projection angles on the patient's breast to the AEC calibrated dosage.

The invention claimed is:

1. A tomosynthesis system for performing an automatic exposure control (AEC) operation, the system comprising:

a processor;

memory including instructions that when executed by the processor cause the processor to:

acquire a scout image of a patient's breast at a first projection angle relative to a 0 degree normal direction to the patient's breast by emitting a scout x-ray dosage towards the patient's breast with the tomosynthesis system, the scout image including a plurality of pixels, wherein each of the plurality of pixels is associated with a detector count value from among a plurality of detector count values;

identify a first region on the scout image as corresponding to a densest portion of the patient's breast;

calculate an average detector count value by averaging the one or more detector count values corresponding to the one or more pixels within the first region;

identify a second region on a first reference image associated with the first projection angle, wherein the second region corresponds to a location on the first reference image that matches a location of the first region on the scout image;

obtain one or more reference detector count values associated with one or more reference pixels within the second region of the first reference image;

calculate an average reference detector count value by averaging the one or more reference detector count values;

based on a ratio between the average reference detector count value and the average detector count value, calculate an AEC calibrated dosage to use in a tomosynthesis scan; and set a radiation dosage for a tomosynthesis sweep at a plurality of projection angles on the patient's breast to the AEC calibrated dosage.

2. The tomosynthesis system of claim 1, wherein obtaining the one or more reference detector count values includes:

extracting the one or more reference detector count values from a reference detector count map associated with the first projection angle, wherein the reference detector count map associated with the first projection angle is one of a plurality of reference detector count maps that are generated in a calibration process prior to acquiring the scout image.

3. The tomosynthesis system of claim 2, wherein the calibration includes:

acquiring a plurality of reference images of a phantom, wherein each of the plurality of reference images is acquired using the tomosynthesis system at each of the plurality of projection angles and each of the plurality of reference images include a plurality of reference image pixels;

determining detector count values corresponding to each of the plurality of reference image pixels within each of the plurality of reference images; and generating the plurality of reference detector count maps corresponding to each of the plurality of projection angles by compiling the plurality of reference image pixels and corresponding detector count values associated with each of the plurality of projection angles.

4. The tomosynthesis system of claim 2, wherein when the first projection angle is not one of the plurality of projection angles that includes the reference detector count map, obtaining the reference detector count values associated with the one or more reference pixels from the second region of the first reference image includes:

estimating the reference detector count values by performing (i) an interpolation function, (ii) an extrapolation function (iii) or a polynomial curve fitting function.

5. The tomosynthesis system of claim 1, wherein the plurality of projection angles includes a range of angles that is between about −60 degrees and about +60 degrees relative to the patient's breast.

6. The tomosynthesis system of claim 1, wherein calculating the AEC calculated dosage includes multiplying the scout x-ray dosage with the ratio between the average reference detector count value and the average detector count value, and a global scaling factor.

7. The tomosynthesis system of claim 1, wherein the scout x-ray dosage includes a combination of: voltage used to generate a radiation from an x-ray source (kV), x-ray cathode to anode tube current (mA) and a length of time(s) to expose the patient to the radiation.

8. The tomosynthesis system of claim 1, wherein the scout x-ray dosage is less than 10% of the AEC calculated dosage.

9. The tomosynthesis system of claim 1, wherein identifying the densest portion of the patient's breast includes:

applying a gain map associated with the first projection angle to the scout image to compensate for angle effects; and identifying pixels within pre-identified center region that includes the lowest detector count values.

10. A method of performing an automatic exposure control (AEC) operation using a tomosynthesis system, the method comprising:

acquiring a scout image of a patient's breast at a first projection angle by emitting a scout x-ray dosage towards the patient's breast with the tomosynthesis system, the scout image including a plurality of pixels, wherein each of the plurality of pixels is associated with a detector count value from among a plurality of detector count values;

identifying a first region on the scout image as corresponding to a densest portion of the patient's breast;

calculating an average detector count value by averaging the one or more detector count values corresponding to the one or more pixels within the first region;

identifying a second region on a first reference image associated with the first projection angle, wherein the second region corresponds to a location on the first reference image that matches a location of the first region on the scout image;

obtaining one or more reference detector count values associated with one or more reference pixels within the second region of the first reference image;

calculating an average reference detector count value by averaging the one or more reference detector count values;

based on a ratio between the average reference detector count value and the average detector count value, calculating an AEC calibrated dosage to use in a tomosynthesis scan; and setting a radiation dosage for a tomosynthesis sweep at a plurality of projection angles on the patient's breast to the AEC calibrated dosage.

11. The method of claim 10, wherein obtaining the one or more reference detector count values includes:

extracting the one or more reference detector count values from a reference detector count map associated with the first projection angle, wherein the reference detector count map associated with the first projection angle is one of a plurality of reference detector count maps that are generated in a calibration process prior to acquiring the scout image.

12. The method of claim 11, wherein the calibration process includes:

acquiring a plurality of reference images of a phantom, wherein each of the plurality of reference images is acquired using the tomosynthesis system at each of the plurality of projection angles and each of the plurality of reference images include a plurality of reference image pixels;

determining reference image detector count values corresponding to each of the plurality of reference image pixels within each of the plurality of reference images; and generating the plurality of reference image detector count maps corresponding to each of the plurality of projection angles by compiling the plurality of reference image pixels and corresponding reference image detector count values associated with each of the plurality of projection angles.

13. The method of claim 11, wherein when the first projection angle is not one of the plurality of projection angles that includes the reference detector count map, obtaining the reference detector count values associated with the one or more reference pixels from the second region of the first reference image includes:

estimating the reference detector count values by performing (i) an interpolation function, (ii) an extrapolation function or (iii) a polynomial curve fitting function.

14. The method of claim 10, wherein the plurality of projection angles includes a range of angles that is between about −60 degrees and about +60 degrees relative to the patient's breast.

15. The method of claim 10, wherein calculating the AEC calculated dosage includes multiplying the scout x-ray dosage with the ratio between the average reference detector count value and the average detector count value, and a global scaling factor.

16. The method of claim 10, wherein the first projection angle is based on a current position of the tomosynthesis system prior to acquiring the scout image.

17. The method of claim 16, wherein the current position is different than 0 degree angle relative to the patient's breast.

18. The method of claim 10, further comprising:

acquiring the scout image of the patient's breast at a second projection angle that is different than the first projection angle.

19. The method of claim 10, wherein identifying the densest portion of the patient's breast includes:

applying a gain map associated with the first projection angle to the scout image to compensate for angle effects; and identifying pixels within pre-identified center region that includes the lowest detector count values.

20. A method of performing a calibration operation associated with an automatic exposure control (AEC) operation using a tomosynthesis system, the method comprising:

acquiring a plurality of reference images of a phantom at a plurality of projection angles, wherein each of the plurality of reference images include a plurality of reference image pixels;

generating a plurality of reference image detector count maps corresponding to each of the plurality of reference images by compiling a plurality of reference image pixels and corresponding reference image detector count values associated for each of the plurality of reference images;

storing the plurality of reference image detector count maps;

acquiring a scout image of a patient's breast at the first projection angle by emitting a scout x-ray dosage towards the patient's breast with the tomosynthesis system, the scout image including a plurality of pixels, wherein each of the plurality of pixels is associated with a detector count value from among a plurality of detector count values;

identifying a first region on the scout image as corresponding to a densest portion of the patient's breast;

calculating an average detector count value by averaging the one or more detector count values corresponding to the one or more pixels within the first region;

identifying a second region on a first reference image associated with a first projection angle, wherein the second region corresponds to a location on the first reference image that matches a location of the first region on the scout image and the first projection angle is one of the plurality of projection angles and the first reference image is one of the plurality of reference images;

obtaining one or more reference detector count values associated with one or more reference pixels within the second region of the first reference image;

calculating an average reference detector count value by averaging the one or more reference detector count values;

based on a ratio between the average reference detector count value and the average detector count value, calculating an AEC calibrated dosage to use in a tomosynthesis scan; and setting a radiation dosage for a tomosynthesis sweep at a plurality of projection angles on the patient's breast to the AEC calibrated dosage.

* * * * *